(12) United States Patent
Hebeisen et al.

(10) Patent No.: US 8,669,254 B2
(45) Date of Patent: Mar. 11, 2014

(54) PYRIDINE, PYRIDAZINE, PYRIMIDINE OR PYRAZINE CARBOXAMIDES AS HDL-CHOLESTEROL RAISING AGENTS

(75) Inventors: Paul Hebeisen, Basel (CH); Stephan Roever, Inzlingen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 17 days.

(21) Appl. No.: 13/314,224

(22) Filed: Dec. 8, 2011

(65) Prior Publication Data

US 2012/0157476 A1 Jun. 21, 2012

(30) Foreign Application Priority Data

Dec. 15, 2010 (EP) .................................. 10195200

(51) Int. Cl.
| | | |
|---|---|---|
| *C07D 213/64* | (2006.01) | |
| *A01N 43/40* | (2006.01) | |
| *C07D 237/14* | (2006.01) | |
| *A01N 43/58* | (2006.01) | |
| *C07D 239/32* | (2006.01) | |
| *A01N 43/54* | (2006.01) | |
| *A61P 3/06* | (2006.01) | |
| *A61P 9/10* | (2006.01) | |
| *A61P 9/00* | (2006.01) | |

(52) U.S. Cl.
USPC ........... 514/247; 514/350; 514/269; 544/239; 544/298; 546/298

(58) Field of Classification Search
USPC .................. 544/239, 298; 514/247, 350, 269; 546/298
See application file for complete search history.

(56) References Cited

U.S. PATENT DOCUMENTS

| | | | |
|---|---|---|---|
| 3,940,418 A | 2/1976 | Hamilton et al. | |
| 4,293,552 A | 10/1981 | Miesel | |
| 5,462,960 A | 10/1995 | Barth et al. | |
| 5,596,106 A | 1/1997 | Cullinan et al. | |
| 5,624,941 A | 4/1997 | Barth et al. | |
| 5,756,524 A | 5/1998 | Riordan et al. | |
| 6,028,084 A | 2/2000 | Barth et al. | |
| 6,355,631 B1 | 3/2002 | Achard et al. | |
| 6,432,984 B1 | 8/2002 | Barth et al. | |
| 6,479,479 B2 | 11/2002 | Achard et al. | |
| 6,509,367 B1 | 1/2003 | Martin et al. | |
| 6,518,264 B2 | 2/2003 | Achard et al. | |
| 6,566,356 B2 | 5/2003 | Achard et al. | |
| 6,734,176 B2 | 5/2004 | Achard et al. | |
| 6,858,603 B2 | 2/2005 | Achard et al. | |
| 6,872,717 B2 | 3/2005 | Achard et al. | |
| 6,906,080 B1 | 6/2005 | Barth et al. | |
| 7,229,999 B2 | 6/2007 | Hebeisen et al. | |
| 7,345,059 B2 | 3/2008 | Barth et al. | |
| 7,812,028 B2 | 10/2010 | Andjelkovic et al. | |
| 7,897,621 B2 | 3/2011 | Hebeisen et al. | |
| 8,088,920 B2 | 1/2012 | Hebeisen et al. | |
| 8,188,093 B2 | 5/2012 | Andjelkovic et al. | |
| 2001/0027193 A1 | 10/2001 | Achard et al. | |
| 2002/0019383 A1 | 2/2002 | Achard et al. | |
| 2002/0035102 A1 | 3/2002 | Achard et al. | |
| 2003/0055033 A1 | 3/2003 | Achard et al. | |
| 2003/0119810 A1 | 6/2003 | Achard et al. | |
| 2003/0162808 A1 | 8/2003 | Achard et al. | |
| 2004/0157823 A1 | 8/2004 | Achard et al. | |
| 2004/0235816 A1 | 11/2004 | Achard et al. | |
| 2004/0259887 A1 | 12/2004 | Dow | |
| 2005/0130953 A1 | 6/2005 | Achard et al. | |
| 2006/0229326 A1 | 10/2006 | Hebeisen et al. | |
| 2007/0293509 A1 | 12/2007 | Hebeisen et al. | |
| 2008/0070931 A1 | 3/2008 | Hebeisen et al. | |
| 2008/0085905 A1 | 4/2008 | Dietz et al. | |
| 2008/0085906 A1 | 4/2008 | Andjelkovic et al. | |
| 2011/0065734 A1* | 3/2011 | Bar et al. .................... | 514/266.4 |

FOREIGN PATENT DOCUMENTS

| | | |
|---|---|---|
| AU | 740486 | 10/1998 |
| AU | 2001/293936 | 4/2001 |
| AU | 2001/237525 | 9/2001 |
| AU | 2001/237526 | 9/2001 |
| EP | 576357 | 12/1993 |
| EP | 656354 | 6/1995 |

(Continued)

OTHER PUBLICATIONS

Munro et al., "Nature" 365:61-65 (1993).
Pacheco et al., "J. Pharmacol. Exp. Ther." 257(1):170-183 (1991).
Shinkai, H., "Mini Reviews in Medicinal Chemistry" 2:271-273 (2002).
Williamson et al., "Drugs" 60(6):1303-1314 (2000).

(Continued)

*Primary Examiner* — James O Wilson
*Assistant Examiner* — Cecilia M Jaisle

(57) ABSTRACT

The present invention relates to compounds of the formula

I

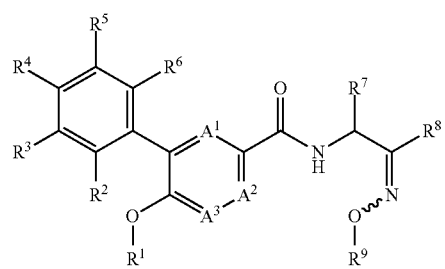

wherein $A^1$ to $A^3$ and $R^1$ to $R^9$ are defined in the description, and to pharmaceutically acceptable salts thereof, their manufacture, pharmaceutical compositions containing them and their use as medicaments for the treatment and/or prophylaxis of diseases which can be treated with HDL-cholesterol raising agents, such as particularly dyslipidemia, atherosclerosis and cardiovascular diseases.

21 Claims, No Drawings

(56) References Cited

FOREIGN PATENT DOCUMENTS

| | | |
|---|---|---|
| IL | 151321 | 11/2008 |
| WO | 96/02248 | 2/1996 |
| WO | 97/19063 | 5/1997 |
| WO | 98/31227 | 7/1998 |
| WO | 98/41519 | 9/1998 |
| WO | 98/43635 | 10/1998 |
| WO | 01/64633 | 9/2001 |
| WO | 01/64634 | 9/2001 |
| WO | 01/70700 | 9/2001 |
| WO | 02/28346 | 4/2002 |
| WO | 03/051850 | 6/2003 |
| WO | 03/051851 | 6/2003 |
| WO | 03/084930 | 10/2003 |
| WO | 2004/110453 | 12/2004 |
| WO | 2004/111033 | 12/2004 |
| WO | 2004/111034 | 12/2004 |
| WO | 2004/111038 | 12/2004 |
| WO | 2004/111039 | 12/2004 |
| WO | 2005/073192 | 8/2005 |
| WO | 2006/106054 | 10/2006 |
| WO | 2007/011760 | 1/2007 |
| WO | 2007/147746 | 12/2007 |
| WO | 2008/031734 | 3/2008 |
| WO | 2008/040649 | 4/2008 |
| WO | 2008/040651 | 4/2008 |
| WO | 03/082191 | 10/2009 |
| WO | 2009/121741 | 10/2009 |
| WO | 2010/051188 | 5/2010 |
| WO | 2011/029827 | 3/2011 |

OTHER PUBLICATIONS

Mechoulam, R., "Cannabinoids as Therapeutic Agents" (CRC Press),:1-20 ( 1986).
Gomaraschi et al., Expert Opin. Ther. Targets 10(4):561-572 ( 2006).
Hackman, BMJ 334:163-164 ( 2007).
Gaoni et al., "J. Am. Chem. Soc." 86:1646 ( 1964).
"English language Abstract corresponding to EP576357" (1993).
Williams et al., "Psychopharmacology" 143(3):315-317 ( 1999).
Pertwee et al., "Life Sci." 56(23-24):1949-1955 ( 1995).
Devane et al., "Science" 258:1946-1949 ( 1992).
Barth et al., "Cannabinoid Antagonists: From Research Tools to Potential New Drugs." Abstracts of Papers, 222nd ACS National Meeting, Chicago, IL, USA (Aug. 26-30, 2001).
Hosohata et al., "Life Sci." 61:115-118 ( 1997).
Ryberg et al., "FEBS Lett." 579:259-264 ( 2005).
Felder et al., "Proc. Natl. Acad. Sci. USA" 90(16):7656-7660 ( 1993).
Pertwee, R. G., "Pharmaceut. Sci." 3(11):539-545 ( 1997).
Pertwee, R. G., "Curr. Med. Chem." 6(8):635-664 ( 1999).
Casiano et al., "NIDA Res. Monogr." 105:295-296 ( 1991).
Dimarzo et al., "Nature" 410(6830):822-825 ( 2001).
Andjelkovic et al., "HCAPLUS: 4410504" ( 2008).
Felder et al., "J. Pharmacol. Exp. Ther." 284:291-297 ( 1998).
Dimarzo et al., "Trends in Neuroscience" 21(12):521-528 ( 1998).
Hackman, D., "JAMA" 296(14):1731-1732 ( 2006).
Porter et al., "Pharmacol. Ther." 90(1):45-60 ( 2001).
Belsey et al., Curr. Med. Res. Opin. 24(09):2703-2709 ( 2008).
Colombo et al., "Life Sci." 63(8):L113-L117 ( 1998).
Shire et al., "Journal of Biological Chemistry" 270:3726-3731 ( 1995).
International Search Report—PCT/EP2011/072392 mailed Feb. 2, 2012.
Kanyonyo et al., "Bioorg. Med. Chem. Lett." 9(15):2233-2236 ( 1999).
Jordan et al., "Nature Reviews" 2:2005 ( 2003).
Ooms et al., "J. Med. Chem." 45(9):1748-1756 ( 2002).
Patani et al., "Bioisosterism: A Rational Approach to Drug Design" Chemical Reviews 96:3147-3176 (1996).

* cited by examiner

PYRIDINE, PYRIDAZINE, PYRIMIDINE OR PYRAZINE CARBOXAMIDES AS HDL-CHOLESTEROL RAISING AGENTS

PRIORITY TO RELATED APPLICATION(S)

This application claims the benefit of European Patent Application No. 10195200.0 filed Dec. 15, 2010, which is hereby incorporated by reference in its entirety.

FIELD OF THE INVENTION

The present invention is concerned with oxime compounds being HDL-cholesterol raising agents, their manufacture, pharmaceutical compositions containing them and their use as therapeutically active substances.

The compounds of the invention are HDL-cholesterol raising agents and can therefore be used in the therapeutic and/or prophylactic treatment of diseases and disorders such as dyslipidemia, atherosclerosis and cardiovascular diseases.

BACKGROUND OF THE INVENTION

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, vascular complications of diabetes, improvement of glycemic control, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

The object of the present invention is therefore to provide compounds that are potent HDL-cholesterol raising agents. It has been found that the compounds of formula I of the present invention are very useful for the treatment and/or prophylaxis of diseases and disorders which can be treated with HDL-cholesterol raising agents, i.e. the compounds of formula I are especially useful for the treatment and/or prevention of dyslipidemia, atherosclerosis and cardiovascular diseases. Object of the present invention is also to provide compounds which are, at therapeutically active concentrations that increase HDL-concentrations, not interacting with the CB1 receptor. This is because CB1 receptor ligands may compromise the therapeutic utility of HDL-cholesterol raising agents, as both agonists and antagonists of the CB1 receptor have the potential to lead to side effects.

SUMMARY OF THE INVENTION

The present invention relates to compounds according to formula I,

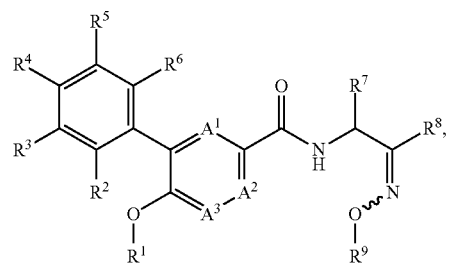

wherein
$A^1, A^2$ and $A^3$ are each individually selected from N and CH, provided that at least one of $A^1$, $A^2$ or $A^3$ is N and at least one of $A^1$, $A^2$ or $A^3$ is CH;
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy and cyano;

$R^7$ and $R^8$ together with the C atoms to which they are attached form a cycloalkyl ring, or $R^7$ is hydrogen and $R^8$ is lower halogenalkyl or cycloalkyl; and $R^9$ is selected from the group consisting of hydrogen, lower alkyl, lower halogenalkyl, lower alkoxyalkyl and lower carbamoylalkyl;

and pharmaceutically acceptable salts thereof.

The present invention also relates to a pharmaceutical composition comprising a compound as described above, or a pharmaceutically acceptable salt thereof, and a pharmaceutically acceptable carrier and/or adjuvant.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, particularly of one to four carbon atom(s).

The term "alkyl", alone or in combination with other groups, refers to a branched or straight-chain monovalent saturated aliphatic hydrocarbon radical of one to twenty carbon atoms, particularly one to sixteen carbon atoms, in particular one to ten carbon atoms.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular ethyl, propyl, isopropyl and tert-butyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, in particular methoxy.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are e.g. —$CH_2$—O—$CH_3$, —$CH_2$—$CH_2$—O—$CH_3$, —$CH_2$—O—$CH_2$—$CH_3$ and the groups specifically exemplified herein. More particularly, lower alkoxyalkyl is methoxyethyl.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Of particular interest are $C_{3-7}$-hydroxyalkyl groups. Examples of lower hydroxyalkyl groups are 2-hydroxybutyl, 3-hydroxy-2,2-dimethylpropyl and the groups specifically exemplified therein.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl, more particularly cyclopropyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest resides cyclopropylmethyl.

The term "halogen" refers to fluoro, chloro, bromo and iodo, with fluoro, chloro and bromo being of particular interest. More particularly, halogen refers to fluoro and chloro.

The term "lower halogenalkyl" or "halogen-$C_{1-7}$-alkyl" refers to lower alkyl groups which are mono- or multiply substituted with halogen, in particular with fluoro or chloro, most particularly with fluoro. Examples of lower halogenalkyl groups are e.g. —$CF_3$, —$CHF_2$, —$CH_2Cl$, —$CH_2CF_3$, —$CH(CF_3)_2$, —$CF_2$—$CF_3$, —$CH_2$—$CH_2$—$CF_3$, —$CH(CH_3)$—$CF_3$ and the groups specifically exemplified herein. Of particular interest are the groups trifluoromethyl (—$CF_3$), 2,2,2-trifluoroethyl (—$CH_2CF_3$), and 1,1,1-trifluoro-propan-2-yl (—$CH(CH_3)$—$CF_3$).

The term "lower halogenalkoxy" or "halogen-$C_{1-7}$-alkoxy" refers to lower alkoxy groups which are mono- or multiply substituted with halogen, in particular with fluoro or chloro, most particularly with fluoro. Examples of lower halogenalkyl groups are e.g. —$OCF_3$, —$OCHF_2$, —$OCH_2Cl$, —$OCH_2CF_3$, —$OCH(CF_3)_2$, —$OCF_2$—$CF_3$ and —$OCH(CH_3)$—$CF_3$ The term "cyano" means to group —CN.

The term "carbamoyl" refers to the group —CO—$NH_2$.

The term "lower carbamoylalkyl" or "carbamoyl-$C_{1-7}$-alkyl" refers to lower alkyl groups as defined above wherein one of the hydrogen atoms of the lower alkyl group is replaced by a carbamoyl group. Examples of lower carbamoylalkyl groups are 3-carbamoylpropyl, 4-carbamoylbutyl and 5-carbamoylpentyl, more particularly 4-carbamoylbutyl.

The term "lower alkylcarbonyl" refers to the group —CO—R", wherein R" is lower alkyl as defined herein before. "Lower alkylcarbonylamino" refers to the group —NH—CO—R", wherein R" is lower alkyl as defined herein before.

The term "lower alkylcarbonylaminoalkyl" or "$C_{1-7}$-alkylcarbonylamino-$C_{1-7}$-alkyl" refers to lower alkyl groups as defined above wherein one of the hydrogen atoms of the lower alkyl group is replaced by a lower alkylcarbonylamino group. An example for a lower alkylcarbonylaminoalkyl group is ethylcarbonylaminoethyl.

The term "lower phenylalkyl" or "phenyl-$C_{1-7}$-alkyl" refers to lower alkyl groups as defined above wherein at least one of the hydrogen atoms of the lower alkyl group is replaced by a phenyl group. In particular, lower phenylalkyl means benzyl.

The term "heterocyclyl" refers to a saturated or partly unsaturated 3-, 4-, 5-, 6- or 7-membered ring which can comprise one, two or three heteroatoms selected from N, O and S. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuranyl, tetrahydrofuranyl, dihydropyranyl, tetrahydropyranyl, and thiomorpholinyl. Of particular interest is the tetrahydrofuranyl group.

The term "lower heterocyclylalkyl" or "heterocyclyl-$C_{1-7}$-alkyl" refers to lower alkyl groups as defined above wherein at least one of the hydrogen atoms of the lower alkyl group is replaced by a heterocyclyl group as defined above.

The term "heteroaryl" refers to an aromatic 5- or 6-membered ring which can comprise one, two or three atoms selected from N, O and S. Examples of heteroaryl groups are e.g. furanyl, pyridyl, pyrazinyl, pyrimidinyl, pyridazinyl, thienyl, isoxazolyl, thiazolyl, isothiazolyl, thiadiazolyl, oxazolyl, imidazolyl, pyrazolyl, triazolyl, oxadiazolyl, oxatriazolyl, tetrazolyl, pentazolyl, or pyrrolyl. The term "heteroaryl" also includes bicyclic groups comprising two 5- or 6-membered rings, in which one or both rings are aromatic and can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl, and 3,4-dihydro-2H-pyrido[3,2-b][1,4]oxazinyl. The heteroaryl group can optionally be mono- or disubstituted by lower alkyl, hydroxy, cyano or halogen. Heteroaryl groups of particular interest are furanyl, oxazolyl, isoxazolyl, pyrazolyl, thiazolyl, isothiazolyl, [1,2,3]thiadiazolyl, pyridyl, pyrazinyl, pyridazinyl, pyrimidinyl and 3,4-dihydro-2H-pyrido[3,2-b][1,4]oxazinyl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above.

"Isomeric forms" are all forms of a compound characterized by having an identical molecular formula but that differ in the nature or the sequence of bonding of their atoms or in the arrangement of their atoms in space. Particularly, the isomeric forms differ in the arrangement of their atoms in space and can also be termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

The term "pharmaceutically acceptable salts" refers to those salts which retain the biological effectiveness and properties of the free bases or free acids, and which do not possess any own properties that are undesirable. The salts are formed with inorganic acids such as hydrochloric acid, hydrobromic acid, sulfuric acid, nitric acid, phosphoric acid and the like, in particular hydrochloric acid, and organic acids such as formic acid, acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. Thus, preferred "pharmaceutically acceptable salts" include the acetate, bromide, chloride, formate, fumarate, maleate, mesylate, nitrate, oxalate, phosphate, sulfate, tartrate and tosylate salt of compounds of formula I. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, diethylamine, lysine, arginine, N-ethylpiperidine, piperidine, piperazine and the like. The compound of formula I can also be present in the form of zwitterions or in the form of hydrates. Particularly preferred pharmaceutically acceptable salts of compounds of formula I are the hydrochloride salts.

The present invention relates to compounds of formula I,

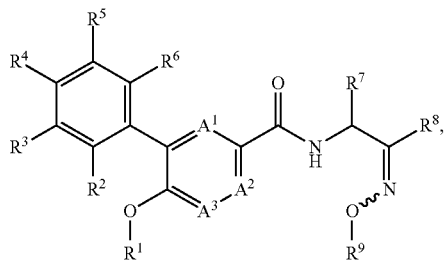

I wherein
$A^1$, $A^2$ and $A^3$ are each individually selected from N and CH, provided that at least one of $A^1$, $A^2$ or $A^3$ is N and at least one of $A^1$, $A^2$ or $A^3$ is CH;

$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy and cyano;
$R^7$ and $R^8$ together with the C atoms to which they are attached form a cycloalkyl ring, or
$R^7$ is hydrogen and $R^8$ is lower halogenalkyl or cycloalkyl; and
$R^9$ is selected from the group consisting of lower alkyl, lower halogenalkyl, lower alkoxyalkyl and lower carbamoylalkyl;
and pharmaceutically acceptable salts thereof.

The invention relates in particular to compounds of formula I, wherein, wherein $R^1$ is lower cycloalkylalkyl or lower halogenalkyl, more particularly to compounds of formula I, wherein $R^1$ is cyclopropylmethyl or lower halogenalkyl. In an embodiment, $R^1$ is lower halogenalkyl, for example 2,2,2-trifluoroethyl or 1,1,1-trifluoro-propan-2-yl. In an embodiment, $R^1$ is 2,2,2-trifluoroethyl.

Compounds of formula I of the invention are those, wherein $R^2$ and $R^6$ are independently from each other hydrogen or halogen. Compounds of formula I, wherein $R^2$ and $R^6$ are hydrogen, are of particular interest.

The invention further relates to compounds of formula I, wherein $R^3$ and $R^5$ are independently from each other selected from the group consisting of hydrogen, lower alkyl, lower alkoxy, halogen, lower halogenalkyl, lower halogenalkoxy and cyano. In particular, the invention relates to compounds of formula I, wherein $R^3$ and $R^5$ are independently from each other hydrogen or halogen, more particularly hydrogen or chloro.

Furthermore, the invention is concerned with compounds of formula I, wherein $R^4$ is selected from the group consisting of hydrogen, lower alkoxy, halogen, lower halogenalkyl, lower halogenalkoxy and cyano. More particularly, $R^4$ is lower alkyl or halogen. Most particularly, $R^4$ is halogen, more specifically chloro.

Compounds of formula I according to the invention are further those, wherein $R^7$ and $R^8$ together with the C atoms to which they are attached form a cycloalkyl ring. More particularly, the invention refers to compounds of formula I, wherein $R^7$ and $R^8$ together with the C atoms to which they are attached form a cyclohexyl ring, i.e. that are compounds of the formula I-I,

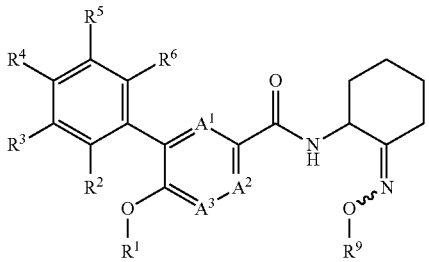

in all its stereoisomeric forms.

Another group of compounds of formula I according to the invention are those, wherein $R^7$ is hydrogen and $R^8$ is lower halogenalkyl or cycloalkyl. In particular, $R^8$ is trifluoromethyl or cyclopropyl.

Compounds of formula I according to the invention are further those, wherein $R^9$ is selected from the group consisting of lower alkyl, lower halogenalkyl, lower alkoxyalkyl and lower carbamoylalkyl. In particular, $R^9$ is lower alkyl, more particularly methyl or isopropyl. $R^9$ groups of particular interest are furthermore selected from 2,2,2-trifluoroethyl, methoxymethyl and carbamoylmethyl.

Furthermore, the invention is concerned with compounds of formula I, wherein $A^3$ is N and $A^1$ and $A^2$ are CH, i.e. pyridine compounds of the formula I-II,

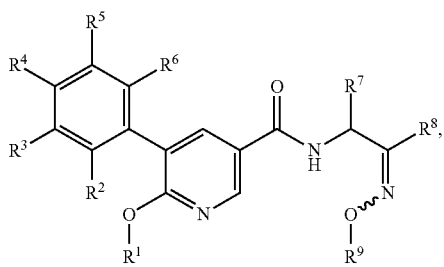

wherein $R^1$ to $R^9$ are as defined herein before.

The invention further relates to compounds of formula I, wherein $A^2$ is N and $A^1$ and $A^3$ are CH, i.e. pyridine compounds of the formula I-III,

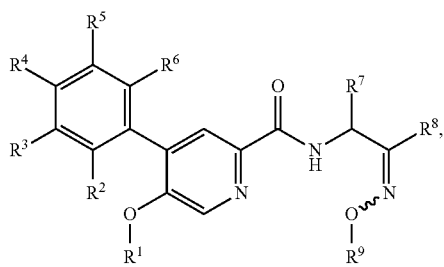

Further compounds of formula I of the invention are those, wherein $A^1$ is N and $A^2$ and $A^3$ are CH, i.e. pyridine compounds of the formula I-IV,

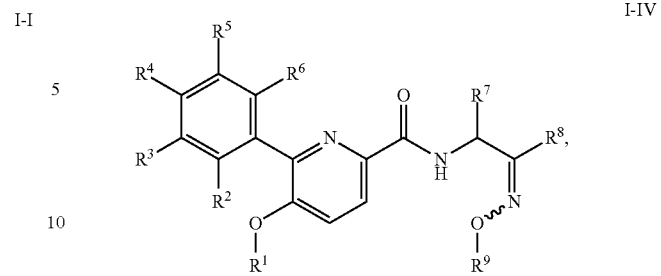

Compounds of formula I according to the present invention are further those, wherein two of $A^1$, $A^2$ and $A^3$ are N and one of $A^1$, $A^2$ or $A^3$ is CH.

In particular, the invention relates to compounds of formula I, wherein $A^2$ and $A^3$ are N and $A^1$ is CH, i.e. pyridazine compounds of the formula I-V,

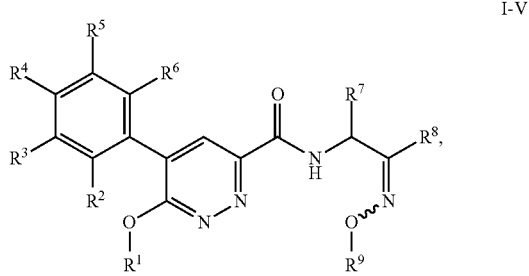

Furthermore, the invention relates to compounds of formula I, wherein $A^1$ and $A^3$ are N and $A^2$ is CH, i.e. pyrazine compounds of the formula I-VI,

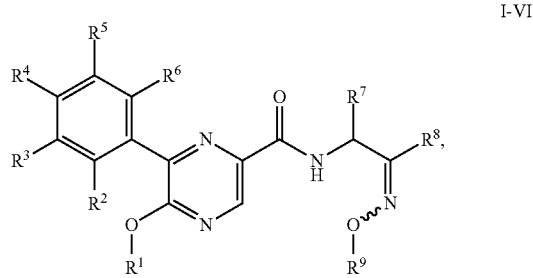

The invention also relates to compounds of formula I, wherein $A^1$ and $A^2$ are N and $A^3$ is CH, i.e. pyrimidine compounds of the formula I-VII,

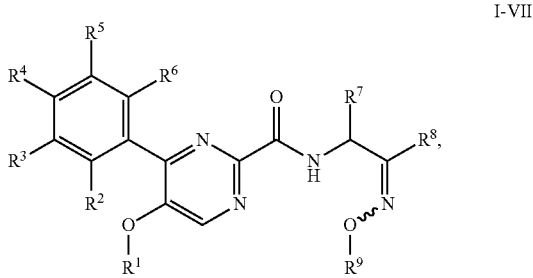

Particular compounds of formula I of the present invention are the following:

5-(4-chloro-phenyl)-6-cyclopropylmethoxy-N-{(S)-2-[(E)-methoxyimino]-cyclohexyl}-nicotinamide,
5-(4-chloro-phenyl)-N-{(S)-2-[(E)-methoxyimino]-cyclohexyl}-6-(2,2,2-trifluoro-ethoxy)-nicotinamide,
5-(4-chloro-phenyl)-6-cyclopropylmethoxy-N-{(S)-2-[(E)-isopropoxyimino]-cyclohexyl}-nicotinamide,
5-(4-chloro-phenyl)-6-cyclopropylmethoxy-N-{(S)-2-[(E)-2,2,2-trifluoro-ethoxyimino]-cyclohexyl}-nicotinamide,
N-{(S)-2-[(E)-carbamoylmethoxyimino]-cyclohexyl}-5-(4-chloro-phenyl)-6-cyclopropylmethoxy-nicotinamide,
5-(4-chloro-phenyl)-6-cyclopropylmethoxy-N-{(S)-2-[(E)-methoxymethoxyimino]-cyclohexyl}-nicotinamide,
5-(3,4-dichloro-phenyl)-N-{(S)-2-[(E)-methoxyimino]-cyclohexyl}-6-(2,2,2-trifluoro-ethoxy)-nicotinamide,
5-(3,4-dichloro-phenyl)-N-{(R)-2-[(E)-methoxyimino]-cyclohexyl}-6-(2,2,2-trifluoro-ethoxy)-nicotinamide,
4-(4-chloro-phenyl)-5-(2,2,2-trifluoro-ethoxy)-pyridine-2-carboxylic acid {(S)-2-[(E)-methoxyimino]-cyclohexyl}-amide,
6-(4-chloro-phenyl)-5-(2,2,2-trifluoro-ethoxy)-pyridine-2-carboxylic acid {(S)-2-[(E)-methoxyimino]-cyclohexyl}-amide,
N-(E)-(2-cyclopropyl-2-hydroxyimino-ethyl)-5-(3,4-dichloro-phenyl)-6-(2,2,2-trifluoro-ethoxy)-nicotinamide,
N-{2-cyclopropyl-2-[(E)-methoxyimino]-ethyl}-5-(3,4-dichloro-phenyl)-6-(2,2,2-trifluoro-ethoxy)-nicotinamide
5-(4-chloro-phenyl)-N-{2-cyclopropyl-2-[(Z)-methoxyimino]-ethyl}-6-(2,2,2-trifluoro-ethoxy)-nicotinamide,
5-(4-chloro-phenyl)-N-{2-cyclopropyl-2-[(E)-methoxyimino]-ethyl}-6-(2,2,2-trifluoro-ethoxy)-nicotinamide,
5-(3,4-dichloro-phenyl)-6-(2,2,2-trifluoro-ethoxy)-N-{3,3,3-trifluoro-2-[(Z)-methoxyimino]-propyl}-nicotinamide,
5-(4-chloro-phenyl)-6-(2,2,2-trifluoro-ethoxy)-pyridazine-3-carboxylic acid {(R)-2-[(E)-methoxyimino]-cyclohexyl}-amide,
5-(4-chloro-phenyl)-6-(2,2,2-trifluoro-ethoxy)-pyridazine-3-carboxylic acid {(S)-2-[(E)-methoxyimino]-cyclohexyl}-amide,
5-(4-chloro-phenyl)-6-cyclopropylmethoxy-pyridazine-3-carboxylic acid {(S)-2-[(E)-methoxyimino]-cyclohexyl}-amide,
4-(4-chloro-phenyl)-5-cyclopropylmethoxy-pyrimidine-2-carboxylic acid {2-cyclopropyl-2-[(Z)-methoxyimino]-ethyl}-amide,
4-(4-chloro-phenyl)-5-cyclopropylmethoxy-pyrimidine-2-carboxylic acid {2-cyclopropyl-2-[(E)-methoxyimino]-ethyl}-amide,
6-(4-chloro-phenyl)-5-(2,2,2-trifluoro-ethoxy)-pyridine-2-carboxylic acid {3,3,3-trifluoro-2-[(Z)-methoxyimino]-propyl}-amide,
N-{2-cyclopropyl-2-[(E/Z)-2,2,2-trifluoro-ethoxyimino]-ethyl}-5-(3,4-dichloro-phenyl)-6-(2,2,2-trifluoro-ethoxy)-nicotinamide,
(E)-N-(2-cyclopropyl-2-(methoxyimino)ethyl)-5-(3,4-dichlorophenyl)-6-(2,2,2-trifluoroethoxy)pyridazine-3-carboxamide,
5-(3,4-dichloro-phenyl)-6-(2,2,2-trifluoro-ethoxy)-pyridazine-3-carboxylic acid {(S)-2-[(E)-methoxyimino]-cyclohexyl}-amide,
(S,E)-5-(4-chlorophenyl)-N-(2-cyclopropyl-2-(methoxyimino)ethyl)-6-(1,1,1-trifluoropropan-2-yloxy)pyridazine-3-carboxamide,
(S,E)-6-(4-chlorophenyl)-N-(2-cyclopropyl-2-(methoxyimino)ethyl)-5-(1,1,1-trifluoropropan-2-yloxy)pyrazine-2-carboxamide,
6-(4-chlorophenyl)-N-((S,E)-2-(methoxyimino)cyclohexyl)-5-((S)-1,1,1-trifluoropropan-2-yloxy)pyrazine-2-carboxamide,
4-(4-chlorophenyl)-N-((S,E)-2-(methoxyimino)cyclohexyl)-5-((S)-1,1,1-trifluoropropan-2-yloxy)pyrimidine-2-carboxamide,
4-(4-chlorophenyl)-N-((S,E)-2-(methoxyimino)cyclohexyl)-5-((S)-1,1,1-trifluoropropan-2-yloxy)picolinamide,
5-(4-chlorophenyl)-N-((S,E)-2-(methoxyimino)cyclohexyl)-6-((S)-1,1,1-trifluoropropan-2-yloxy)nicotinamide,
5-(4-chloro-phenyl)-N-{2-cyclopropyl-2-[(E)-methoxyimino]-ethyl}-6-((S)-2,2,2-trifluoro-1-methyl-ethoxy)-nicotinamide,
(E)-4-(4-chlorophenyl)-N-(2-cyclopropyl-2-(methoxyimino)ethyl)-5-(2,2,2-trifluoroethoxy)picolinamide, and
pharmaceutically acceptable salts thereof.

Particularly advantageous compounds of formula I of the present invention are the following:
(E)-N-(2-cyclopropyl-2-(methoxyimino)ethyl)-5-(3,4-dichlorophenyl)-6-(2,2,2-trifluoroethoxy)pyridazine-3-carboxamide,
(S,E)-6-(4-chlorophenyl)-N-(2-cyclopropyl-2-(methoxyimino)ethyl)-5-(1,1,1-trifluoropropan-2-yloxy)pyrazine-2-carboxamide,
4-(4-chlorophenyl)-N-((S,E)-2-(methoxyimino)cyclohexyl)-5-((S)-1,1,1-trifluoropropan-2-yloxy)pyrimidine-2-carboxamide, and
5-(4-chlorophenyl)-N-((S,E)-2-(methoxyimino)cyclohexyl)-6-((S)-1,1,1-trifluoropropan-2-yloxy)nicotinamide,
and pharmaceutically acceptable salts thereof.

The compounds of formula I can be prepared by a process, which process comprises the steps
a) oxidation of a compound of formula

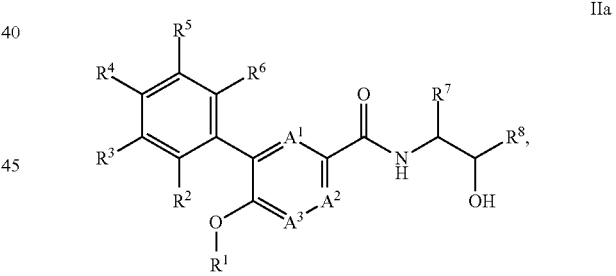

IIa wherein $A^1$ to $A^3$ and $R^1$ to $R^8$ are as defined herein before, with an oxidizing agent to obtain a ketone of the formula

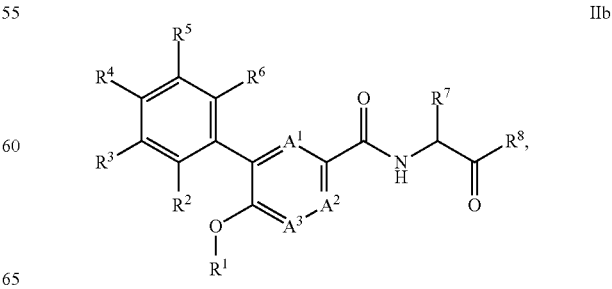

IIb wherein $A^1$ to $A^3$ and $R^1$ to $R^8$ are as defined hereinbefore, and b) condensation of the compound of formula IIb with an oxyamino compound of formula

III wherein $R^{9'}$ is hydrogen or lower alkyl, to obtain a compound of formula

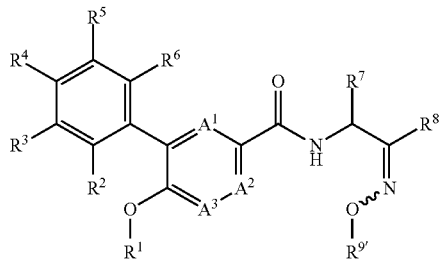

Ia wherein $A^1$ to $A^3$ and $R^1$ to $R^8$ are as defined in claim 1 and $R^{9'}$ is hydrogen or lower alkyl, and optionally, in case $R^{9'}$ is hydrogen, c) alkylation of the compound of formula I with a common alkylating agent to obtain a compound of formula

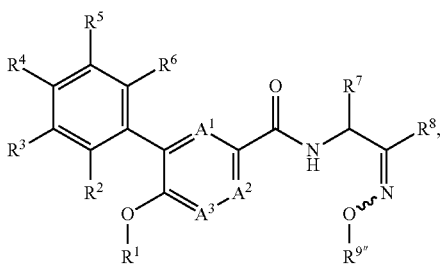

Ib wherein $R^{9'''}$ is selected from the group consisting of lower alkyl, lower halogenalkyl, lower alkoxyalkyl and lower carbamoylalkyl, and d) if desired, conversion of the resulting compound of formula I into a pharmaceutically acceptable salt thereof.

A suitable oxidizing agent for the reaction of compounds of formula IIa is for example Dess Martin periodinane.

The present invention also relates to a process for the manufacture of compounds of formula I as defined above, which process comprises coupling a compound of formula

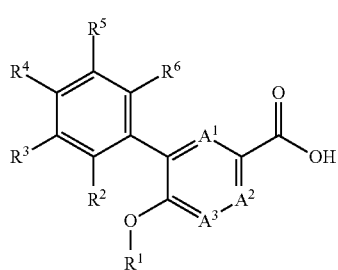

IV wherein $A^1$ to $A^3$ and $R^1$ to $R^6$ are as defined herein before, with an amine of the formula

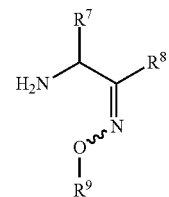

V wherein $R^7$, $R^8$ and $R^9$ are as defined herein before, with the help of a coupling agent under basic conditions, and, if desired, converting the resulting compound of formula I into a pharmaceutically acceptable salt thereof.

Coupling agents for the reaction of compounds of the general formula IV with amines of the general formula V are for example (1-chloro-2-methyl-propenyl)-dimethyl-amine, N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). Preferred coupling agent is (1-chloro-2-methyl-propenyl)-dimethyl-amine. Suitable bases include triethylamine, diisopropylethylamine and, particularly, Hünig's base.

The synthesis of the compounds of the general formula I can be accomplished according to the following schemes.

Following the procedure according to scheme 1, compound AA (6-chloro-5-hydroxy-4-iodo-2-pyridinemethanol, CAS RN 208519-37-3) can be used as starting material. AA is commercially available or can alternatively be prepared by a two step sequence from 2-chloro-3-pyridinol following literature procedures.

Compounds of the general formula AB can be prepared from the compound of the formula AA by reaction with a suitably substituted primary or secondary alkylhalide $R^1$—X or primary or secondary alkyltrifluoromethanesulfonate $R^1$—OTf in the presence of a base, for example sodium hydride, in a inert solvent, for example hexamethylphosphoramide, at temperatures from room temperature to reflux temperature of the solvent, in particular at elevated temperature, e.g. 120° C.

Compounds of the general formula AC can be prepared from compounds of the general formula AB by coupling a suitably substituted aryl metal species of the general AF, in particular a arylboronic acid or arylboronic acid ester, with compounds of the general formula AB in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base, particularly triethylamine or sodium carbonate in an inert solvent such as dimethylformamide or toluene.

Scheme 1

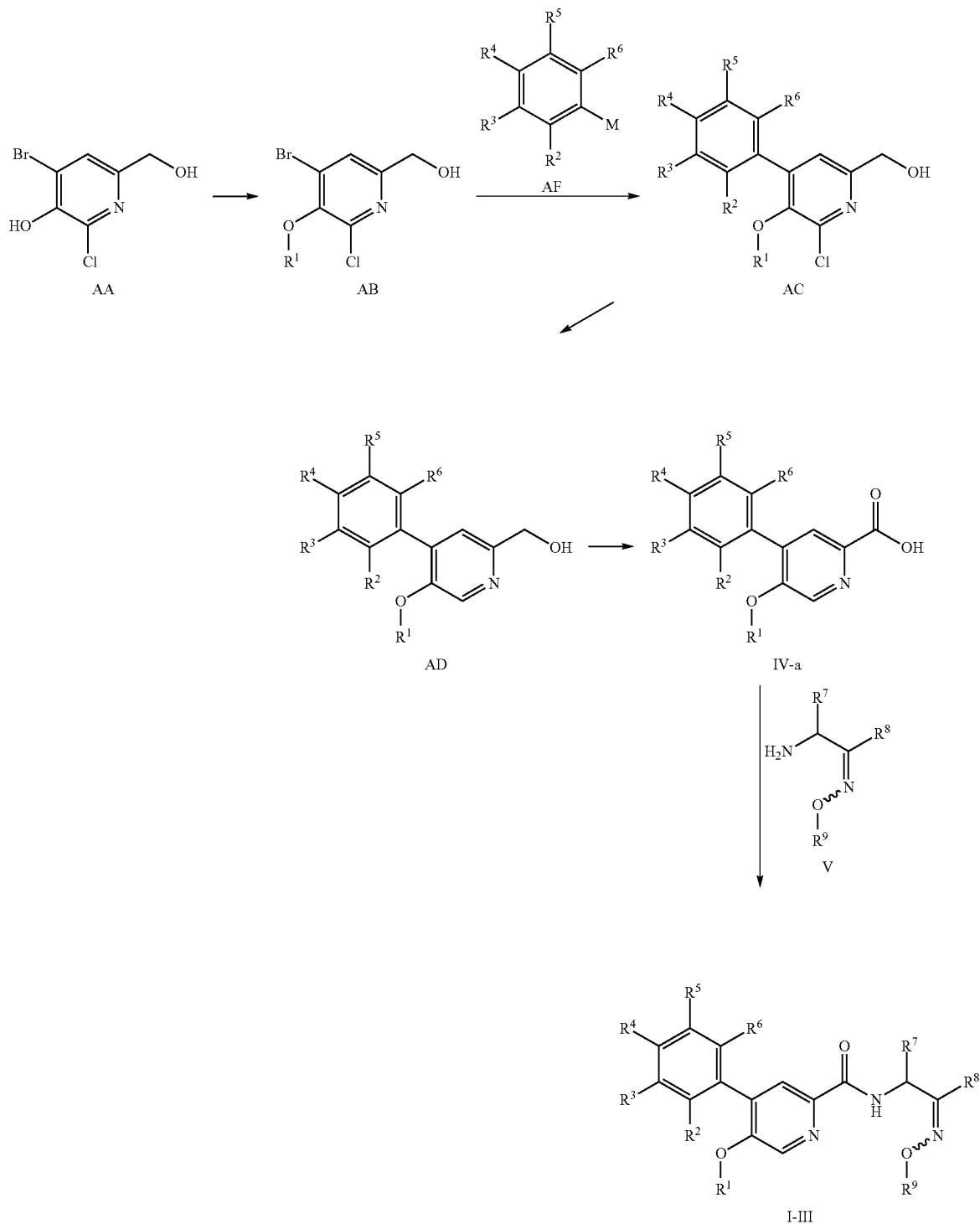

Compounds of the general formula AD can be obtained by selective hydrogenation of compounds of the general formula AC by methods known in the art, for example by hydrogenation with zinc in acetic acid in the presence of tetramethylammonium bromide at temperatures from room temperature to reflux temperature of the solvent, in particular at a temperature of 50° C.

Compounds of the general formula IV-a can be prepared from compounds of the general formula AD by oxidation using the vast array of possibilities known in the art. A convenient method is the use of a TEMPO (2,2,6,6-tetramethylpiperidine-1-oxyl radical) catalyzed oxidation with a sodiumchlorite-sodiumhypochlorite mixture in a suitable solvent mixture, particularly in acetonitrile/phosphate buffer mixtures, at temperatures from room temperature to elevated temperatures, more particularly at 35° C.

Compounds of the general formula I-III can be prepared from compounds of the general formula IV-a and the corresponding amine of the general formula V by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), (1-chloro-2-methyl-propenyl)-dimethyl-amine and O-benzotriazol-1-yl-N,N,N',N'-tetramethyluronium tetrafluoroborate (TBTU) can be employed to affect such transformation. A convenient method is to use for example TBTU and a base, for example Hünig's base (N-ethyldiisopropylamine) in an inert solvent such as for example dimethylformamide at room temperature. Another practical method is the use of (1-chloro-2-methyl-propenyl)-dimethyl-amine and a base, for example Hünig's base (N-ethyldiisopropylamine) in an inert solvent such as for example dichloromethane.

Following the procedure according to scheme 2, compound BA (5-bromo-6-chloro-3-pyridinecarboxylic acid methylester, CAS RN 78686-77) can be used as starting material. BA is commercially available or can alternatively be prepared by a multi step sequence from 6-hydroxy-3-pyridinecarboxylic acid following literature procedures.

Compound of the general formula BB can be prepared from BA by coupling a suitably substituted aryl metal species of the general formula AF, in particular an arylboronic acid or arylboronic acid ester, with BA in the presence of a suitable catalyst, particularly a palladium catalyst and more particularly palladium(II)acetate/triphenylphosphine mixtures or palladium(II)chloride-dppf (1,1'-bis(diphenylphosphino)ferrocene) complexes and a base, particularly triethylamine or sodium carbonate in an inert solvent such as dimethylformamide or toluene.

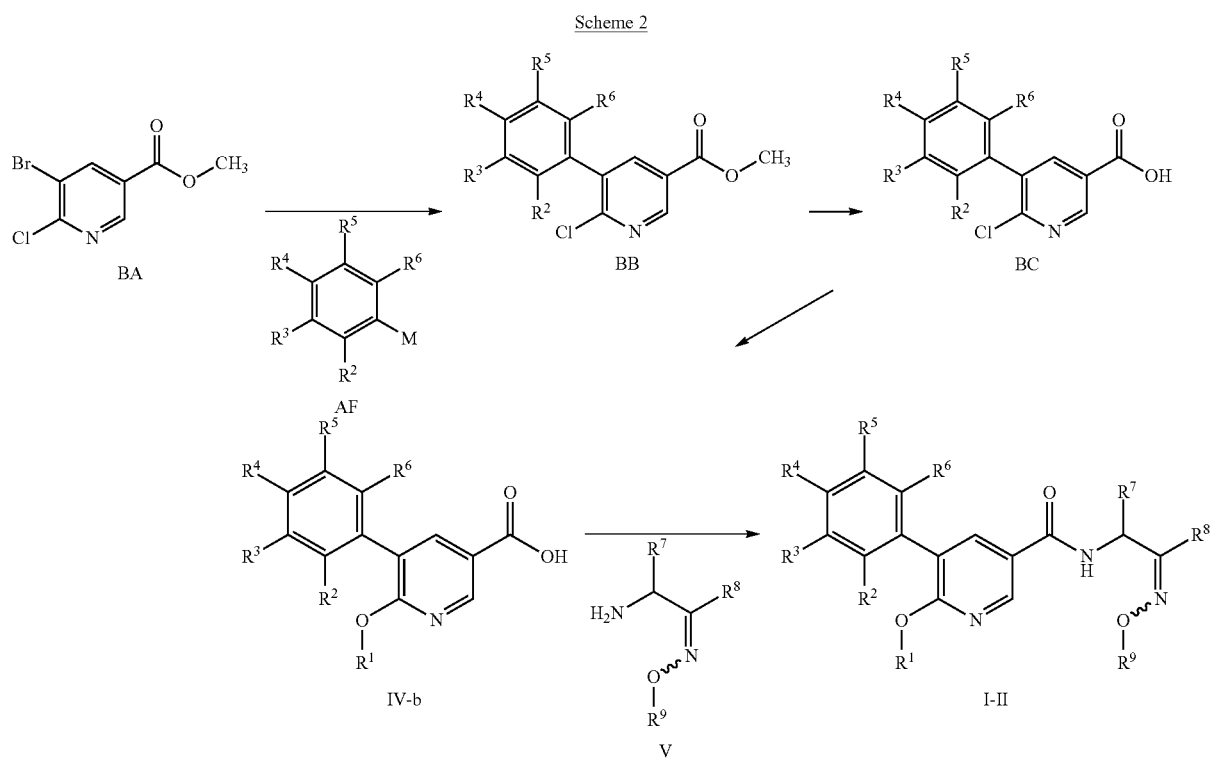

Scheme 2

Compounds of the general formula BC can be obtained by saponification of compounds of the general formula BB by methods known in the art, for example by saponification with an alkalimetal hydroxide, for example lithium hydroxide, in a suitable solvent, for example a mixture of THF and water.

Compounds of the general formula IV-b can be prepared from compounds of the general formula BC by reaction with a suitably substituted primary or secondary alcohol $R^1$—OH, more specifically with 2,2,2-trifluoroethanol, (S)-1,1,1-trifluoro-propan-2-ol and cyclopropylmethanol, in the presence of a base, for example potassium hydroxide or sodium hydride, in an inert solvent, for example dimethylsulfoxide, at temperatures from room temperature to reflux temperature of the solvent, in particular at room temperature.

Compounds of the general formula I-III can be prepared from compounds of the general formula IV-b and the corresponding amine of the general formula V by suitable amide bond forming reactions described above.

Following the procedure according to scheme 3, compound CA (2,6-dichloro-3-fluoro-pyridine CAS RN 52208-50-1) can be used as starting material. CA is commercially available.

Scheme 3

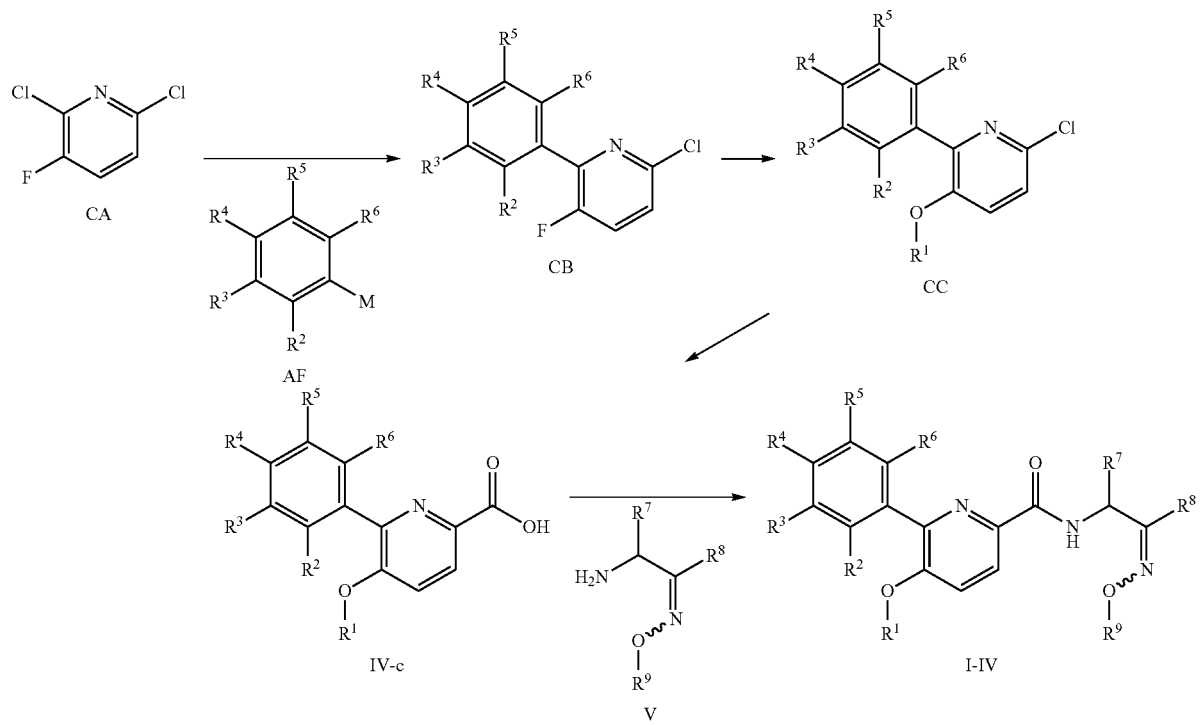

Compounds of the general formula CB can be prepared from compound CA by coupling a suitably substituted aryl metal species of the general formula AF, in particular an arylboronic acid or arylboronic acid ester, with compounds of the general formula CA in the presence of a suitable catalyst, particularly a palladium catalyst and more particularly palladium(II)acetate/triphenylphosphine mixtures or palladium (II)chloride-dppf (1,1'-bis(diphenylphosphino) ferrocene) complexes and a base, particularly triethylamine or sodium carbonate in an inert solvent such as dimethylformamide, toluene, tetrahydrofuran, water or acetonitrile, in particular tetrahydrofuran and mixtures of tetrahydrofuran and water.

Compounds of the general formula CC can be obtained from compounds of the general formula CB by reaction with an alcohol of the general formula $R^1OH$, more specifically with 2,2,2-trifluoroethanol, (S)-1,1,1-trifluoro-propan-2-ol and cyclopropylmethanol, in the presence of a suitable base such as sodium hydroxide, sodium hydride and cesium carbonate in an inert solvent such as tetrahydrofuran, dimethylformamide or dimethylsulfoxide, particularly dimethylsulfoxide at temperature between −20° C. to reflux, particularly at room temperature.

Compounds of the general formula IV-c can be obtained from compounds of the general formula CC by transition metal catalyzed, more specifically palladium catalyzed, preferentially palladium(II)chloride-dppf catalyzed reaction with carbon monoxide in a suitable solvent such as a primary alcohol, particularly methanol, at pressures of carbon monoxide of 1-200 bar, particularly 1-70 bar and temperatures of 0-150° C., in particular 1-100° C. followed of saponification of the resulting ester by methods well known to the ones skilled in the art.

Compounds of the general formula I-IV can be prepared from compounds of the general formula IV-c and the corresponding amine of the general formula V by suitable amide bond forming reactions described above.

Following the procedure according to scheme 4, certain compounds of the general formula DA (e.g. 3-chloro-6-methoxy-pyridazine CAS RN 1722-10-7), that are commercially available, can be used as starting materials. Alternatively compounds of the general formula DA can be obtained from 3,6-dichloro-pyridazine (CAS RN 141-30-0) by reaction with an alcohol of the general formula $R^1OH$, more specifically more specifically with 2,2,2-trifluoroethanol, (S)-1,1,1-trifluoro-propan-2-ol and cyclopropylmethanol, in the presence of a suitable base such as sodium hydroxide, sodium hydride and cesium carbonate in an inert solvent such as tetrahydrofuran, dimethylformamide or dimethylsulfoxide, particularly dimethylsulfoxide at temperatures between −20° C. to reflux, more particularly at room temperature.

Compounds of the general formula DB can be obtained from compounds of the general formula DA by ortho directed metallation using a suitable base such as LDA or lithium 2,2,6,6-tetramethylpiperidide in an inert solvent such as tetrahydrofuran at low temperatures, in particular −110 to −78° C. followed by reaction with iodine at low temperatures, particularly −110 to −78° C.

Compounds of the general formula DC can be obtained by coupling a suitably substituted aryl metal species of the general formula AF, in particular an arylboronic acid or arylboronic acid ester, with compounds of the general formula DB in the presence of a suitable catalyst, particularly a palladium catalyst and more particularly palladium(II)acetate/triphenylphosphine mixtures or palladium(II)chloride-dppf (1,1'-bis(diphenylphosphino)ferrocene) complexes and a base, in particular triethylamine or sodium carbonate in an inert solvent such as dimethylformamide, toluene, tetrahydrofuran or acetonitrile, particularly tetrahydrofuran.

Compounds of the general formula IV-d can be obtained from compounds of the general formula DC by palladium acetate catalyzed reaction with carbon monoxide in a suitable solvent such as a primary alcohol, particularly methanol, at pressures of carbon monoxide of 1-200 bar, particularly 1-70 bar and temperatures of 0 to 150° C., particularly 1 to 100° C., followed by saponification of the resulting ester by methods well known to the ones skilled in the art.

preferentially PdCl$_2$.dppf catalyzed, reaction with carbon monoxide in a suitable solvent such as a primary alcohol particularly methanol at pressures of carbon monoxide of 1 to 200 bar, particularly 1 to 70 bar, and temperatures of 0 to 150° C., particularly 0 to 120° C.

Compounds of the general formula DF can be obtained from compounds of the general formula DE by reaction with

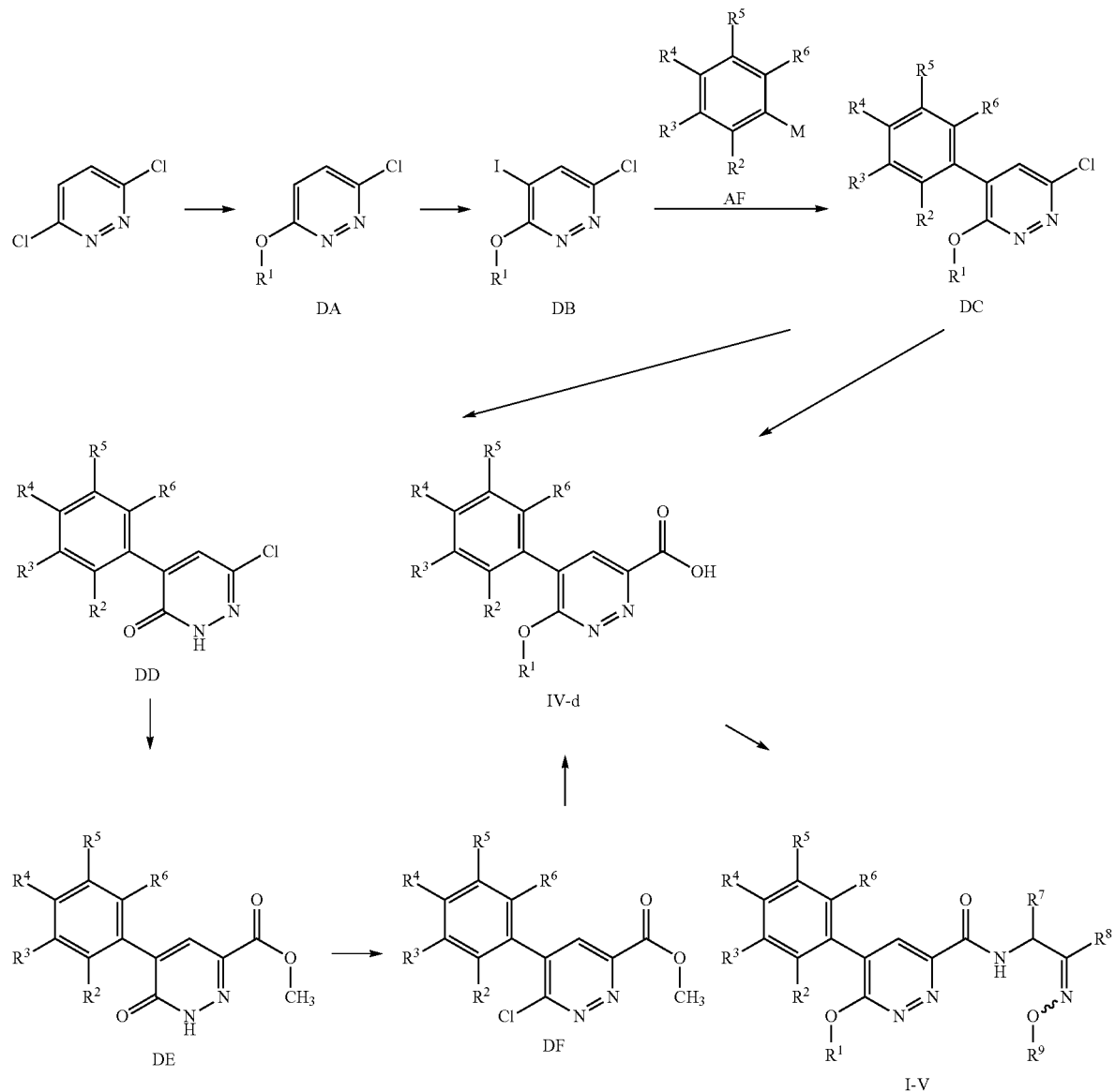

Scheme 4

Ether side chains R$^1$O that are incompatible with the above described ortho directed metallation protocol, such as trifluoroethyl ethers can alternatively be introduced according to scheme 4 by reactions of compounds with the formula DC, in which R$^1$ represents a simple alkyl group such as methyl or cyclopropylmethyl, with suitable acids such as hydrochloric acid in an inert solvent such as dioxane to yield compounds of the general formula DD.

Compounds of the general formula DE can be obtained from compounds of the general formula DD by Pd catalyzed, a chlorinating agent such as phosphoroxychloride in a suitable solvent or neat at temperatures ranging from room temperature to reflux.

Compounds of the general formula IV-d can be obtained from compounds of the general formula DF by reaction with an alcohol of the general formula R$^1$OH, more specifically with 2,2,2-trifluoroethanol, (S)-1,1,1-trifluoro-propan-2-ol and cyclopropylmethanol, in the presence of a suitable base such cesium carbonate in an inert solvent such as 2,2,2-trifluoroethanol, tetrahydrofuran, dimethylformamide or dimethylsulfoxide, particularly dimethylsulfoxide, at temperatures between −20° C. to reflux, particularly at room temperature followed by saponification of the resulting ester by methods well known to the ones skilled in the art.

Compounds of the general formula I-V can be prepared from compounds of the general formula IV-d and the corresponding amine of the general formula V by suitable amide bond forming reactions described above.

Following the procedure according to scheme 5,2,4-dichloro-5-fluoro-pyrimidine (CAS RN 2927-71-1) can be used as starting material for the preparation of compound of the general formula EA by coupling with a suitably substituted aryl metal species of the general formula AF, in particular an arylboronic acid or arylboronic acid ester in the presence of a suitable catalyst, particularly a palladium catalyst and more particularly palladium(II)acetate/triphenylphosphine mixtures or palladium(II)chloride-dppf (1,1'-bis(diphenylphosphino)ferrocene) complexes and a base, particularly triethylamine or sodium carbonate in an inert solvent such as dimethylformamide, toluene, tetrahydrofuran or acetonitrile, more particularly in mixtures of tetrahydrofuran and water.

Compounds of the general formula EB can be obtained from compounds of the general formula EA by reaction with an alcohol of the general formula R$^1$OH, more specifically with 2,2,2-trifluoroethanol and cyclopropylmethanol, in the presence of a suitable base such as sodium hydroxide, sodium hydride and cesium carbonate in an inert solvent such as tetrahydrofuran, dimethylformamide or dimethylsulfoxide, particularly dimethylsulfoxide, at temperatures between −20° C. to reflux, particularly at room temperature.

Compounds of the general formula IV-e can be obtained from compounds of the general formula EB by palladium (preferentially PdCl$_2$.dppf) catalyzed reaction with carbon monoxide in a suitable solvent such as a primary alcohol, particularly methanol, at pressures of carbon monoxide of 1 to 200 bar, particularly 1 to 70 bar, and temperatures of 0 to 150° C., particularly 0 to 120° C., followed by saponification of the resulting ester by methods well known to the ones skilled in the art.

Compounds of the general formula I-VII can be prepared from compounds of the general formula IV-e and the corresponding amine of the general formula V by suitable amide bond forming reactions described above.

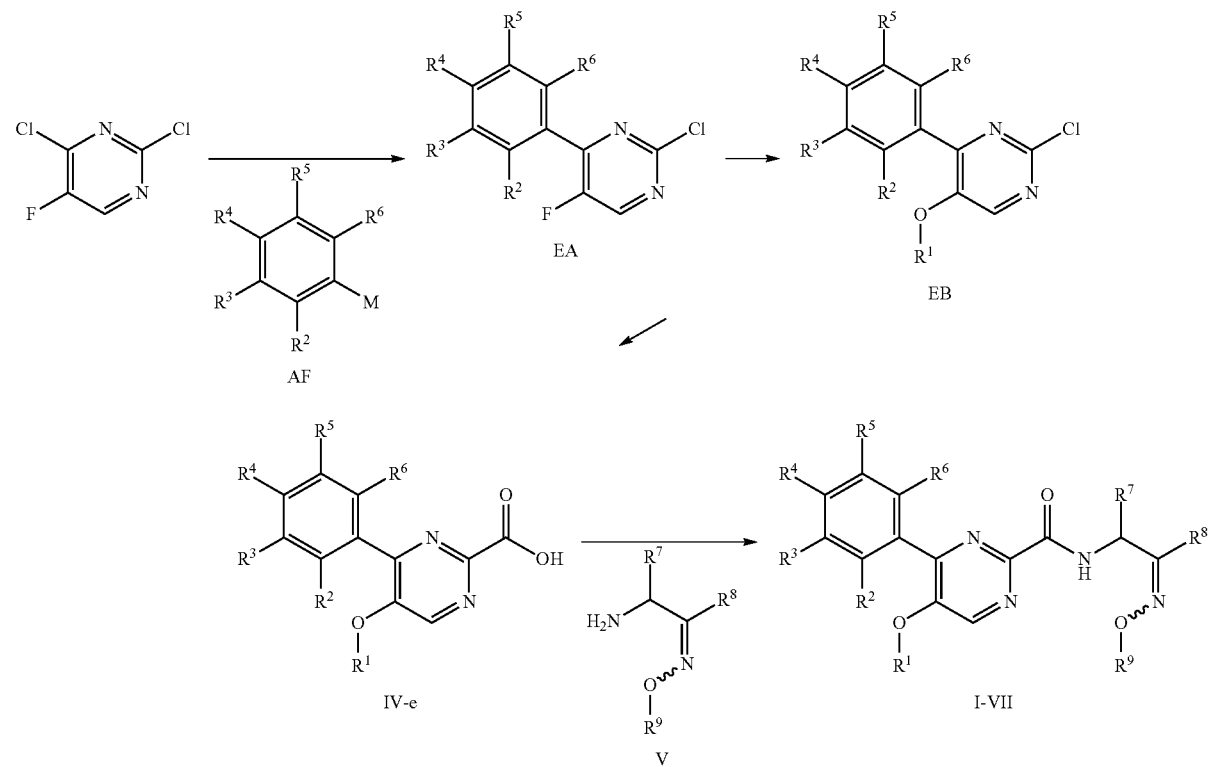

Scheme 5

According to scheme 6, compounds of the general formula I-VI can be prepared from compounds of the general formula IV-f and the corresponding amine of the general formula V by suitable amide bond forming reactions described above. Following the procedure according to scheme 6, compounds of the general formula IV-f can be obtained from compound F (CAS 960247-79-4,5-bromo-6-(4-chlorophenyl)-2-pyrazinecarboxylic acid methyl ester) by reaction with an alcohol of the general formula R$^1$OH, more specifically with 2,2,2-trifluoroethanol, (S)-1,1,1-trifluoro-propan-2-ol and cyclopropylmethanol, in the presence of a suitable base such as sodium hydroxide, sodium hydride and cesium carbonate in an inert solvent such as tetrahydrofuran, dimethylformamide or dimethylsulfoxide, particularly dimethylsulfoxide, at temperatures between −20° C. to reflux, in particular at room temperature.

Scheme 6

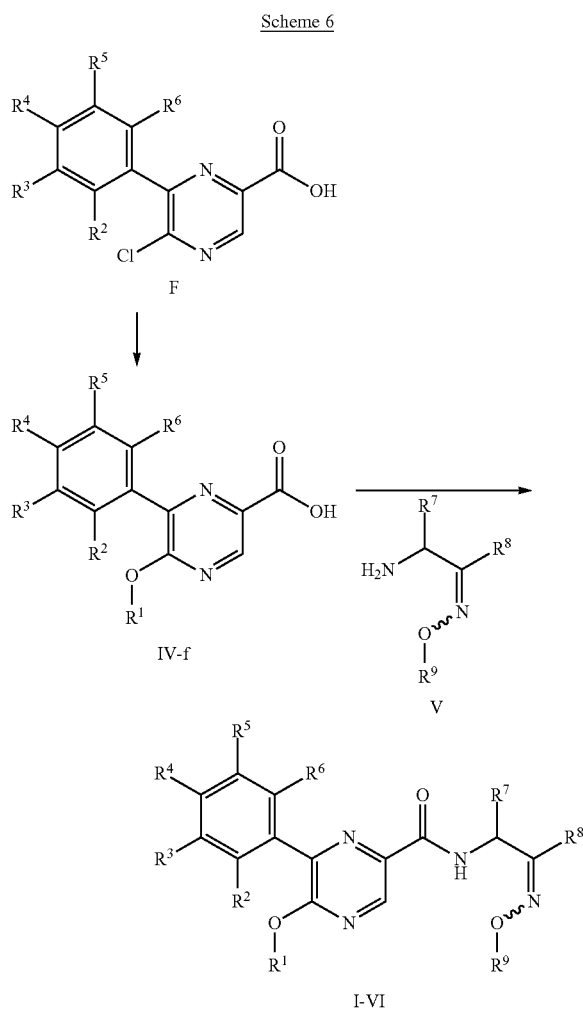

As described above, the compounds of formula I of the present invention or pharmaceutically acceptable salts thereof can be used as medicaments for the treatment and/or prophylaxis of diseases which can be treated with HDL-cholesterol raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, vascular complications of diabetes, improvement of glycemic control, obesity or endotoxemia. The use as medicament for the treatment and/or prevention of dyslipidemia, atherosclerosis and cardiovascular diseases is of particular interest.

The invention therefore also relates to pharmaceutical compositions comprising a compound of formula I as defined above and a pharmaceutically acceptable carrier and/or adjuvant. The pharmaceutical compositions are useful in the treatment and/or prophylaxis of diseases which can be treated with HDL-cholesterol raising agents.

Thus, the invention relates to a pharmaceutical composition as defined above for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, vascular complications of diabetes, improvement of glycemic control, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I or a pharmaceutically acceptable salt thereof to a patient in need thereof. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, vascular complications of diabetes, improvement of glycemic control, obesity or endotoxemia. A method for the treatment and/or prophylaxis of dyslipidemia, atherosclerosis and cardiovascular diseases is preferred.

The invention also relates to the compounds of formula I or pharmaceutically acceptable salts thereof for use as medicaments. More specifically, the invention relates to compounds of formula I for use as HDL-cholesterol raising agents. Thus, the invention is concerned with compounds of formula I for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, vascular complications of diabetes, improvement of glycemic control, obesity or endotoxemia, in particular for use in the treatment and/or prophylaxis of dyslipidemia, atherosclerosis and cardiovascular diseases.

In addition, the invention relates to the use of compounds of formula I as defined above for the preparation of a medicament for the treatment and/or prophylaxis of diseases can be treated with HDL raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, vascular complications of diabetes, improvement of glycemic control, obesity or endotoxemia. The use of compounds of formula I as defined above for the preparation of medicaments for the treatment and/or prophylaxis of dyslipidemia, atherosclerosis and cardiovascular diseases is of particular interest.

In addition, HDL raising agents of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The invention therefore also relates to pharmaceutical compositions comprising a compound of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant, as well as a pharmaceutically acceptable carrier and/or adjuvant.

The invention further relates to compounds of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant for use in the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, vascular complications of diabetes, improvement of glycemic control, obesity or endotoxemia.

The invention also relates to a method for the treatment and/or prophylaxis of diseases which can be treated with HDL-cholesterol raising agents, which method comprises administration of a therapeutically effective amount of a compound according to formula I in combination or association with a therapeutically effective amount of a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

Pharmaceutical Compositions

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is of particular interest.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1-100 mg, particularly 5-50 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example C2

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Pharmacological Tests

The following tests were carried out in order to determine the activity of the compounds of formula I and their valuable pharmacological properties.

Detection of Upregulation of ABCA1 Protein in Cells

The ability of compounds of the invention to increase the level of ABCA1 protein is determined in replicate cultures of THP-1 macrophage cells in 96-well microplates. Cells are plated at an initial density of 100,000 cells/well in 100 µl medium and differentiated to adherent macrophages with the addition of PMA (100 nM) for 68 hrs in 10% fetal bovine serum, 3 µl/L of b-mercaptoethanol, RPMI-1640 medium. Then, cells are incubated with RPMI-1640 medium containing 1% FCS, 25 µg/ml acetylated LDL, for 24 hours at 37°. Following incubation with acetylated LDL, cells are washed twice with 50 µl PBS and incubated with 100 µl of RPMI-1640 medium containing the compound of interest solubilized in DMSO for an additional 24 hrs. The final DMSO concentration in presence of cells is maintained at 0.5%. ApoA-I binding assay using High Content Image Analysis is initiated by replacing with fresh medium, RPMI without Phenol Red, 0.2% BSA containing AlexaFluor®647 labeled ApoA-I for 2 h/37° C./5% CO2. Then, cells are fixed with 4% Formaldehyde in PBS (15 min, RT). Following Nuclei are stained with Hoechst solution (3 µM PBS) and Cytoplasm with Cell Mask Blue (2 µg/ml PBS), 15 min, RT. Finally the stained cells are fixed with a second round of formaldehyde treatment. Fixed stained cells are washed and kept in PBS at 4° C. and can be read immediately until one month after preparation. That the binding of ApoA-I indeed reflected the level of ABCA1 in the cell, was demonstrated by loss of signal when ABCA1 expression was artificially reduced by transfection with small interfering RNA's.

The Alexa Fluor 647-labeled Apolipoprotein A-I (20 nM) was prepared as follows: Human recombinant Apolipoprotein A-I (ApoA-I) was exchanged to a buffer of 0.02 M $NaHCO_3$ at pH 8.2 on an NAP desalting column (GE Healthcare) and brought to a concentration to 40 µM (1.13 mg/ml) by adjustment with the same buffer. The ApoA-I was fluorescently labeled by incubation with Alexa Fluor carboxylic acid succimidyl ester (Alexa Fluor 647, Invitrogen A-20006) at a 2:1 molar ratio (Alexa to ApoA-I) for 1 h under shaking at RT. The remaining unconjugated label was removed by buffer exchange to 0.02M $NaHCO_3$ at pH 8.2.

Imaging and data collection were performed on an OPERA confocal microplate imaging reader using a 20× water immersion objective and UV360 or 405 laser to identify the cell nuclei and a 635 laser to identify the fluorescent ApoA-I. Eight fields of view are captured per well. Image capture and analysis was performed with the Acapella software. Background fluorescence detected in control wells without ApoA-I was subtracted.

Using XLfit3 program (ID Business Solutions Ltd. UK), the model 205 for Dose Response One Site is used to calculate the $EC_{50}$ values. The compounds of the present invention exhibit $EC_{50}$ values in a range of 0.1 µM to 10 µM in the ABCA1 protein detection assay. Particularly, the compounds of the present invention have $EC_{50}$ values in a range of 0.1 µM to 3 µM.

TABLE 1

ABCA1 Protein Increasing Efficacy

| Example | % increase of ABCA1 at 3 µM | $EC_{50}$ [µM] |
|---|---|---|
| 1 | 87.2% @ 3 µM | 0.7 |
| 2 | 88.3% @ 3 µM | 1.82 |
| 3 | 66.4% @ 3 µM | |
| 4 | 90.4% @ 3 µM | |
| 5 | 65.2% @ 3 µM | 2.02 |
| 6 | 71.9% @ 3 µM | |
| 7 | 84.6% @ 3 µM | 4.72 |
| 8 | 63% @ 3 µM | 0.81 |
| 9 | 71.7% @ 3 µM | |
| 10 | 45.6% @ 3 µM | 1.53 |
| 11 | 55.9% @ 3 µM | |
| 12 | 88.4% @ 3 µM | |
| 13 | 66.2% @ 3 µM | |
| 14 | 157.2% @ 3 µM | |
| 15 | 50.5% @ 3 µM | |
| 16 | 55.3% @ 3 µM | 10 |
| 17 | 76.5% @ 3 µM | 2.63 |
| 18 | 57.3% @ 3 µM | 4.99 |
| 19 | 84.2% @ 3 µM | |
| 20 | 87.03% @ 3 µM | |
| 21 | 50% @ 3 µM | |
| 22 | 74% @ 3 µM | |
| 23 | 88% @ 3 µM | 0.54 |
| 24 | 85% @ 3 µM | |
| 25 | 61% @ 3 µM | |
| 26 | 79% @ 3 µM | 1.12 |
| 27 | 65% @ 3 µM | |

TABLE 1-continued

ABCA1 Protein Increasing Efficacy

| Example | % increase of ABCA1 at 3 μM | EC$_{50}$ [μM] |
|---|---|---|
| 28 | 86.5% @ 3 μM | 0.78 |
| 29 | 53.4% @ 3 μM | |
| 30 | 91.3% @ 3 μM | 0.18 |
| 31 | 74.5% @ 3 μM | |
| 32 | 53% @ 3 μM | |

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 μl/L of b-mercaptoethanol, RPMI-1640 medium. Cells are washed once with RPMI-1640 and loaded with RPMI-1640 medium containing 2% FCS, 50 μg/ml acetylated LDL, and 10 μCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 μg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and EC$_{50}$ values were determined.

The compounds of the present invention exhibit EC$_{50}$ values in a range of 0.1 μM to 3.0 μM in the cholesterol efflux assay. Particularly, the compounds of the present invention have EC$_{50}$ values in a range of 0.1 μM to 1.5 μM.

CB1 and CB2 Receptor Affinity

The affinity of the compounds of the invention for cannabinoid receptors was determined using membrane preparations of human embryonic kidney (HEK) cells in which the human CB1 receptor is transiently transfected using a Semliki Forest Virus system in conjunction with [3H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The affinity of the compounds of the invention for cannabinoid CB2 receptors was determined using membrane preparations of human embryonic kidney (HEK) cells in which the human CB2 receptor is transiently transfected using a Semliki Forest Virus system in conjunction with [$^3$H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The ability of the compounds to displace the radioligand [$^3$H]-CP-55,940 was measured at a concentration of 10 μM and values provided as [% inhibition @ 10 μM] both for the CB 1 and CB2 receptor assay, The lower % inhibition is, the lower the likelihood of side effects based on CB1 or CB2 receptor inhibition is.

The compounds of the present invention exhibit values below 50% inhibition in both the CB1 and CB2 receptor assay at a concentration of 10 μM. Particularly, the compounds of the present invention exhibit values below 35% inhibition in both the CB1 and CB2 receptor assays and even more particularly below 20% in both assays.

TABLE 2

CB1 and CB2-receptor Affinity

| Example | CB1 receptor affinity [% inhibition @ 10 μM] | CB2 receptor affinity [% inhibition @ 10 μM] |
|---|---|---|
| 1 | 33.96 | 17.23 |
| 2 | 30.75 | 3.53 |
| 3 | 45.67 | 6.86 |
| 4 | 48.48 | 8.91 |
| 5 | 33.13 | 15.07 |
| 6 | 36.71 | 19.16 |
| 7 | 10.54 | 3.56 |
| 8 | 35.18 | 13.07 |
| 9 | 15.91 | 37.61 |
| 10 | 0.74 | 19.24 |
| 11 | 30.02 | 44.27 |
| 12 | 26.78 | 47.72 |
| 13 | 48.58 | 1.52 |
| 14 | 48.17 | 20.91 |
| 15 | 31.96 | 23.22 |
| 16 | 25.44 | 16.55 |
| 17 | 16.55 | 13.57 |
| 18 | 26.86 | 32.45 |
| 19 | 27.96 | 63.79 |
| 20 | 28.76 | 71.65 |
| 21 | 41 | 31 |
| 22 | 36 | 9 |
| 23 | −2 | 14 |
| 24 | 22 | 31 |
| 25 | 39 | 29 |
| 26 | 13 | 9 |
| 27 | 21 | 21 |
| 28 | 34.4 | 18 |
| 29 | 35.5 | 33 |
| 30 | 24.1 | 12.7 |
| 31 | 39.3 | 3.6 |
| 32 | 15 | 29 |

Further demonstration of biological activities of the compounds of the present invention may be accomplished through the following in vivo assays that are well known in the art.

Effects on Plasma Lipid Levels in Lean, Chow Fed Rats

The effects of compounds of compounds of formula I on plasma lipid levels were determined in lean, chow-fed Sprague-Dawley rats with compounds administered by p.o. gavage. After one week of acclimatisation, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague-Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4 h after food was removed. Plasma was separated from blood by low speed centrifugation and selected organs were taken (e.g liver, fat). Total cholesterol, HDL-cholesterol, and triglycerides were determined by measuring total cholesterol, HDL-cholesterol, LDL-cholesterol and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Cholesterol/Fat Fed Hamsters

Efficacy of compounds in modulating plasma lipid levels was determined in hamsters after 5 days of daily administration of compounds. Male hamsters of 6-8 weeks of age were used in the studies. After one week of acclimatisation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol was also determined after selective precipitation of HDL from plasma by standard procedures.

EXAMPLES

MS=mass spectrometry; EI=electron impact; ISP=ion spray, corresponds to ESI (electrospray); NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; HPLC=LC=high performance liquid chromatography, Rt=retention time, tlc=thin layer chromatography, dppf=1,1'-bis(diphenylphosphino)ferrocene, TBTU=O-(benzotriazol-1-yl)-N,N,N',N'-tetramethyl-uronium-tetrafluoroborate; TEMPO=2,2,6,6-tetra-methylpiperidine 1-oxyl radical, DMF=dimethylformamide, DMSO=dimethyl-sulfoxide, THF=tetrahydrofuran.

Example 1

5-(4-Chloro-phenyl)-6-cyclopropylmethoxy-N-{(S)-2-[(E)-methoxyimino]-cyclohexyl}-nicotinamide

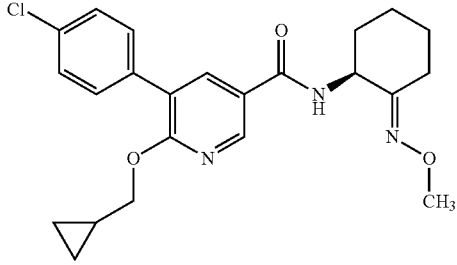 [SMILES: CO/N=C1\CCCC[C@@H]1NC(=O)c1cnc(OCC2CC2)c(-c2ccc(Cl)cc2)c1]

To a solution under of 100 mg of 5-(4-chloro-phenyl)-6-cyclopropylmethoxy-N-((S)-2-oxo-cyclohexyl)-nicotinamide in 1 ml methanol was added 105 mg O-methylhydroxylamine hydrochloride and the mixture was stirred at room temperature for 18 h. The reaction mixture was partitioned between water and ethyl acetate. The phases were separated and the organic phase was purified by chromatography on silica gel using a gradient of heptane:ethyl acetate=95:5 to 50:50 to yield 0.039 g of the title compound as white foam. MS (EI): 402.3 (M+H).

The starting material was prepared as follows.

Example 1b 5-(4-Chloro-phenyl)-6-cyclopropylmethoxy-N-((S)-2-oxo-cyclohexyl)-nicotinamide

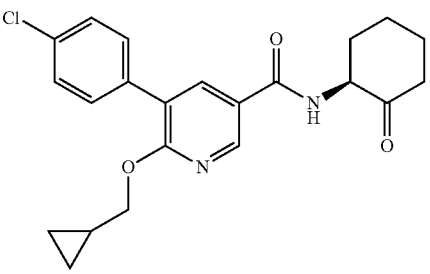 [SMILES: O=C(N[C@H]1CCCCC1=O)c1cnc(OCC2CC2)c(-c2ccc(Cl)cc2)c1]

To a solution of 1.651 g 5-(4-chloro-phenyl)-6-cyclopropylmethoxy-N-((1S,2R)-2-hydroxy-cyclohexyl)-nicotinamide in 25 ml methylene chloride, was added 2.62 g Dess-Martin periodinane as 15% solution in dichloromethane. The reaction mixture was stirred at room temperature for 18 h. The solvent was evaporated and the residue was purified by chromatography on silica gel using a gradient of heptane:ethyl acetate=95:5 to 40:60 to yield 1.46 g of the title compound as white foam. MS (EI): 399.1 (M+H).

Example 2

5-(4-Chloro-phenyl)-N-{(S)-2-[(E)-methoxyimino]-cyclohexyl}-6-(2,2,2-trifluoro-ethoxy)-nicotinamide

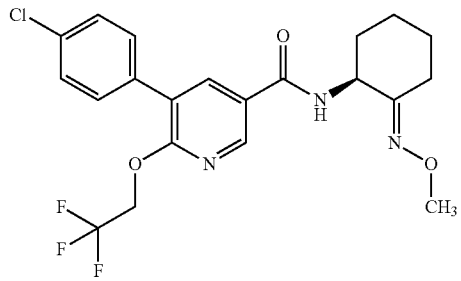 [SMILES: CO/N=C1\CCCC[C@@H]1NC(=O)c1cnc(OCC(F)(F)F)c(-c2ccc(Cl)cc2)c1]

The title compound was obtained as white solid in analogy to Example 1 by substituting 5-(4-chloro-phenyl)-6-cyclopropylmethoxy-N-((S)-2-oxo-cyclohexyl)-nicotinamide with 5-(4-chloro-phenyl)-N-((S)-2-oxo-cyclohexyl)-6-(2,2,2-trifluoro-ethoxy)-nicotinamide. MS (EI): 456.1 (M+H).

Example 2b 5-(4-Chloro-phenyl)-N-((S)-2-oxo-cyclohexyl)-6-(2,2,2-trifluoro-ethoxy)-nicotinamide

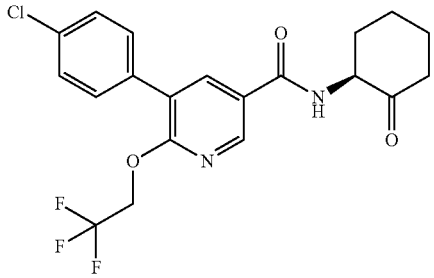 [SMILES: O=C(N[C@H]1CCCCC1=O)c1cnc(OCC(F)(F)F)c(-c2ccc(Cl)cc2)c1]

The starting material 5-(4-chloro-phenyl)-N-((S)-2-oxo-cyclohexyl)-6-(2,2,2-trifluoro-ethoxy)-nicotinamide was obtained from 5-(4-chloro-phenyl)-N-((1S,2R)-2-hydroxy-cyclohexyl)-6-(2,2,2-trifluoro-ethoxy)-nicotinamide as white foam in analogy to Example 1b. MS (EI): 427.1 (M+H)

Example 3

5-(4-Chloro-phenyl)-6-cyclopropylmethoxy-N-{(S)-2-[(E)-isopropoxyimino]-cyclohexyl}-nicotinamide

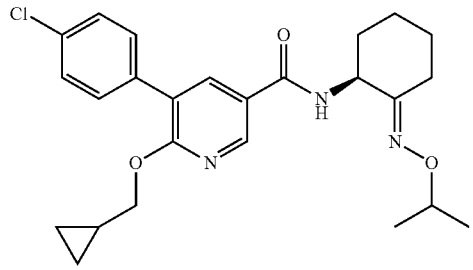 [SMILES: CC(C)O/N=C1\CCCC[C@@H]1NC(=O)c1cnc(OCC2CC2)c(-c2ccc(Cl)cc2)c1]

The title compound was obtained as white foam in analogy to Example 1 by substituting O-methylhydroxylamine hydrochloride with O-isopropyl-hydroxylamine hydrochloride. MS (EI): 456.2 (M+H).

Example 4

5-(4-Chloro-phenyl)-6-cyclopropylmethoxy-N-{(S)-2-[(E)-2,2,2-trifluoro-ethoxyimino]-cyclohexyl}-nicotinamide

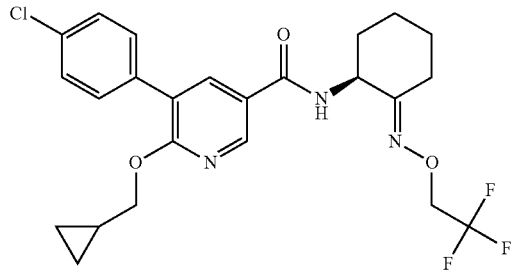 [SMILES: O=C(N[C@H]1CCCC/C1=N\OCC(F)(F)F)c1cnc(OCC2CC2)c(-c2ccc(Cl)cc2)c1]

To a solution of 0.100 g 5-(4-chloro-phenyl)-6-cyclopropylmethoxy-N-{(S)-2-[(E)-hydroxyimino]-cyclohexyl}-nicotinamide in 1.0 ml dimethylformamide was added 0.012 g sodium hydride 55% in oil and the mixture was stirred at room temperature for 30 min. To the resulting solution was added 0.037 ml (0.062 g, 1.1 equivalents) 2,2,2-trifluoroethyl-trifluoro-methanesulfonate and the mixture was stirred at room temperature for 18 h. The reaction mixture was partitioned between water and ethyl acetate. The phases were separated and the organic phase was purified by chromatography on silica gel using a gradient of heptane:ethyl acetate=95:5 to 50:50 to yield 0.040 g of the title compound as light yellow oil. MS (EI): 496.3 (M+H).

The starting material 5-(4-chloro-phenyl)-6-cyclopropylmethoxy-N-{(S)-2-[(E)-hydroxyimino]-cyclohexyl}-nicotinamide was obtained as white solid in analogy to Example 1 by substituting O-methylhydroxylamine hydrochloride with hydroxylamine hydrochloride. MS (EI): 414.2 (M+H).

Example 5

N-{(S)-2-[(E)-Carbamoylmethoxyimino]-cyclohexyl}-5-(4-chloro-phenyl)-6-cyclopropylmethoxy-nicotinamide

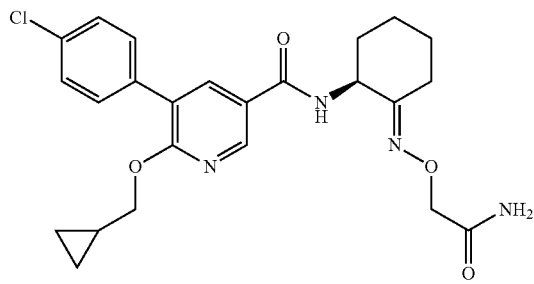 [SMILES: NC(=O)CO/N=C1\CCCC[C@@H]1NC(=O)c1cnc(OCC2CC2)c(-c2ccc(Cl)cc2)c1]

The title compound was obtained as white foam in analogy to Example 4 by substituting 2,2,2-trifluoroethyl trifluoromethanesulfonate with iodoacetamide. MS (EI): 471.2 (M+H).

Example 6

5-(4-Chloro-phenyl)-6-cyclopropylmethoxy-N-{(S)-2-[(E)-methoxymethoxyimino]-cyclohexyl}-nicotinamide

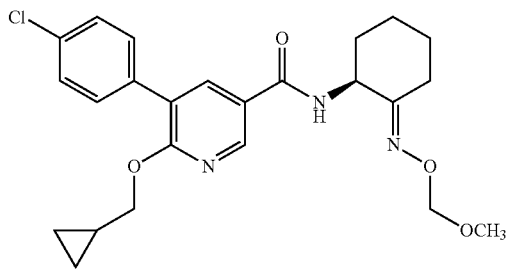 [SMILES: COCO/N=C1\CCCC[C@@H]1NC(=O)c1cnc(OCC2CC2)c(-c2ccc(Cl)cc2)c1]

The title compound was obtained as white foam in analogy to Example 1 by substituting O-methylhydroxylamine hydrochloride with O-methoxymethyl-hydroxylamine hydrochloride. MS (EI): 458.2 (M+H)

Example 7

5-(3,4-Dichloro-phenyl)-N-{(S)-2-[(E)-methoxyimino]-cyclohexyl}-6-(2,2,2-trifluoro-ethoxy)-nicotinamide

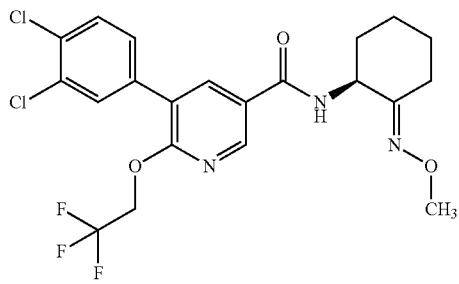 [SMILES: CO/N=C1\CCCC[C@@H]1NC(=O)c1cnc(OCC(F)(F)F)c(-c2ccc(Cl)c(Cl)c2)c1]

The title compound was obtained as white solid in analogy to Example 2 by substituting 5-(4-chloro-phenyl)-N-((S)-2-oxo-cyclohexyl)-6-(2,2,2-trifluoro-ethoxy)-nicotinamide with 5-(3,4-dichloro-phenyl)-N-((S)-2-oxo-cyclohexyl)-6-(2,2,2-trifluoro-ethoxy)-nicotinamide. MS (EI): 490.1 (M+H).

The starting material 5-(3,4-dichloro-phenyl)-N-((S)-2-oxo-cyclohexyl)-6-(2,2,2-trifluoro-ethoxy)-nicotinamide was obtained from 5-(3,4-dichloro-phenyl)-N-((1S,2R)-2-hydroxy-cyclohexyl)-6-(2,2,2-trifluoro-ethoxy)-nicotinamide as white foam in analogy to Example 1b. MS (EI): 461.2 (M+H).

Example 8

5-(3,4-Dichloro-phenyl)-N-{(R)-2-[(E)-methoxyimino]-cyclohexyl}-6-(2,2,2-trifluoro-ethoxy)-nicotinamide

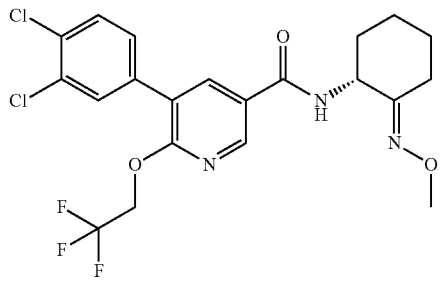 [SMILES: CO/N=C1\CCCC[C@H]1NC(=O)c1cnc(OCC(F)(F)F)c(-c2ccc(Cl)c(Cl)c2)c1]

The title compound was obtained as white solid in analogy to Example 2 by substituting 5-(4-chloro-phenyl)-N-((S)-2-oxo-cyclohexyl)-6-(2,2,2-trifluoro-ethoxy)-nicotinamide with 5-(3,4-dichloro-phenyl)-N-((R)-2-oxo-cyclohexyl)-6-(2,2,2-trifluoro-ethoxy)-nicotinamide. MS (EI): 490.1 (M+H).

The starting material was prepared as follows:

Example 8b 5-(3,4-Dichloro-phenyl)-N-((R)-2-oxo-cyclohexyl)-6-(2,2,2-trifluoro-ethoxy)-nicotinamide

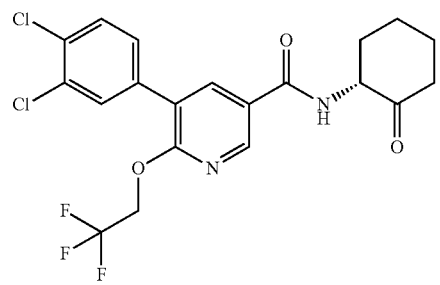 [SMILES: O=C(N[C@@H]1CCCCC1=O)c1cnc(OCC(F)(F)F)c(-c2ccc(Cl)c(Cl)c2)c1]

In analogy to Example 1b by substituting 5-(3,4-dichloro-phenyl)-N-((1R,2S)-2-hydroxy-cyclohexyl)-6-(2,2,2-trifluoro-ethoxy)-nicotinamide for 5-(4-chloro-phenyl)-6-cyclopropylmethoxy-N-((1S,2R)-2-hydroxy-cyclohexyl)-nicotinamide the title compound was obtained as white foam. MS (EI): 461.2 (M+H).

Example 9

4-(4-Chloro-phenyl)-5-(2,2,2-trifluoro-ethoxy)-pyridine-2-carboxylic acid {(S)-2-[(E)-methoxyimino]-cyclohexyl}-amide

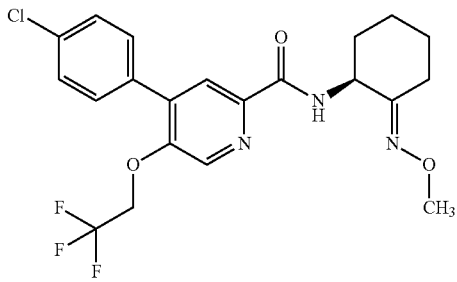

To a solution of 0.050 g 4-(4-chloro-phenyl)-5-(2,2,2-trifluoro-ethoxy)-pyridine-2-carboxylic acid in 2.0 ml dimethylformamide was added 0.030 g (S)-2-amino-cyclohexanone-(E)-O-methyl-oxime hydrochloride, 0.053 g TBTU and 0.097 g N,N-diisopropyl ethyl amine and the mixture was stirred at room temperature for 16 h. The solvent was evaporated under high vacuum and the residue was purified by chromatography on silica gel with a gradient of heptane to ethyl acetate to yield 0.045 g of the title compound as colorless oil. MS (EI): 465.1 (M+H).

The starting materials were obtained as follows:

Example 9b

(S)-2-Amino-cyclohexanone-(E)-O-methyl-oxime hydrochloride

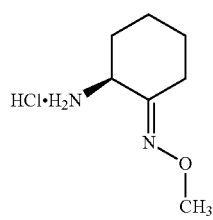

To a solution of 2.13 g ((S)-2-oxo-cyclohexyl)-carbamic acid tert-butyl ester in 10 ml methanol was added 0.46 g O-methylhydroxylamine hydrochloride and the mixture was heated to reflux for 18 h. To the resulting yellow solution was added 2.0 ml of a 4M solution of hydrochloric acid in dioxane and the mixture was refluxed for 30 min. The reaction mixture was evaporated and dried under high vacuum. The semisolid residue was triturated under acetonitrile. The solid was collected by filtration and dried to constant weight under high vacuum to yield 1.25 g of the title compound as white crystals. MS (EI): 142 (M+H).

Example 9c

4-(4-Chloro-phenyl)-5-(2,2,2-trifluoro-ethoxy)-pyridine-2-carboxylic acid

To a solution of [4-(4-chloro-phenyl)-5-(2,2,2-trifluoro-ethoxy)-pyridin-2-yl]-methanol (17.4 g, 55 mmol) in acetonitrile (235 mL), phosphate buffer (pH 6.7, 220 mL) and 2,2,6,6-tetra-methylpiperidine 1-oxyl radical (TEMPO, 0.6 g) was added and the solution was warmed to 35° C. To this warm solution under argon was added with stirring over 2 h simultaneously a solution of NaOCl$_2$ (12.4 g) in water (58 mL) and NaOCl (0.85 mL, 10% solution) in water (35 mL). Stirring was continued for 20 h at 35° C. after which time the solution was cooled to room temperature and quenched by addition of in sequence water (420 mL), 2 N NaOH solution (65 mL) and Na$_2$SO$_3$ solution (17.1 g in 285 mL water). This mixture was stirred for 30 min and acidified with 2 N HCl (175 mL). The mixture was extracted once with ethyl acetate/THF (800/150 mL), and once with ethyl acetate (500 mL). Organic phases were washed with brine (800 mL), pooled and dried with Na$_2$SO$_4$. The solvent phase was concentrated to a volume of ~100 mL. n-Heptane (150 mL) was added and the solvent phase was concentrated again to ~100 mL. This was repeated twice. n-Heptane (100 mL) was added. The product precipitated upon stirring, was filtered off and dried to give the title compound as a white solid (18.4 g, quant.), LC-MS (peak area/EIC) ~100%, 332.0 (M+H)$^+$.

[4-(4-Chloro-phenyl)-5-(2,2,2-trifluoro-ethoxy)-pyridin-2-yl]-methanol was prepared by the following procedure:

Example 9d

[4-Bromo-6-chloro-5-(2,2,2-trifluoro-ethoxy)-pyridin-2-yl]-methanol

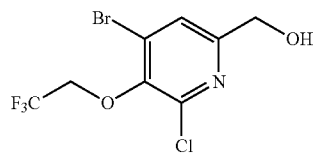 [SMILES: OCc1cc(Br)c(OCC(F)(F)F)c(Cl)n1]

6-Chloro-5-hydroxy-4-iodo-2-pyridinemethanol (CAS Registry No. 208519-37-3) (21.5 g, 75 mmol) was dissolved in hexamethylphosphoramide (210 mL). Over a period of 30 min sodium hydride (3.0 g of 60% dispersion in oil, ~75 mmol) was added with stirring at room temperature. The mixture was stirred for another 45 min at room temperature and 2,2,2-trifluoroethane sulfonate (12.5 mL, 90 mmol) was added drop wise with stirring and temperature control (<40° C.). The mixture was stirred for 18 h at 120° C., cooled to room temperature and poured into water (800 mL). The mixture was acidified with 2N HCl (50 mL) and extracted with ethyl acetate (2×350 mL). Organic phases were washed with water (2×400 mL), pooled and dried with Na$_2$SO$_4$. Solvents were evaporated and the brown, solid residue (27.9 g) was purified by chromatography on silica with ethyl acetate/n-heptane (1:1) to give the title compound as a white solid (24.8 g, 90%), LC-MS (peak area/EIC) 100%, 367.9 (M+H)$^+$.

Example 9e

6-Chloro-4-(4-chloro-phenyl)-5-(2,2,2-trifluoro-ethoxy)-pyridin-2-yl]-methanol

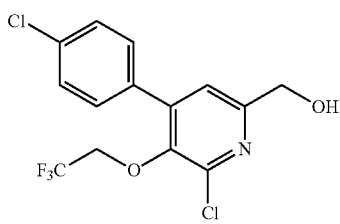 [SMILES: OCc1cc(-c2ccc(Cl)cc2)c(OCC(F)(F)F)c(Cl)n1]

To a suspension of [4-bromo-6-chloro-5-(2,2,2-trifluoro-ethoxy)-pyridin-2-yl]-methanol (24.7 g, 67 mmol) in toluene (300 mL) under argon was added [1,1'-bis(diphenylphosphino)-ferrocene]palladium(II) dichloride dichloromethane adduct (1.65 g, 2 mmol), 4-chlorophenyl-boronic acid (10.5 g, 67 mmol) and 2.0 M Na$_2$CO$_3$-solution (67.2 mL, 134 mmol) with stirring. The mixture was stirred for 90 min at 90° C. and cooled to room temperature. Water (150 mL) was added and the mixture was extracted with ethyl acetate (2×150 mL). Organic phases were pooled and dried with Na$_2$SO$_4$. Solvents were evaporated and the brown, oily residue (27.7 g) was purified by chromatography on silica with ethyl acetate/n-heptane (1:2) to give the title compound as a brown oil (24.1 g, quant), LC-MS (peak area/EIC) ~100%, 352.0 (M+H)$^+$.

Example 9f

[4-(4-Chloro-phenyl)-5-(2,2,2-trifluoro-ethoxy)-pyridin-2-yl]-methanol

A solution of 6-chloro-4-(4-chloro-phenyl)-5-(2,2,2-trifluoro-ethoxy)-pyridin-2-yl]-methanol (24.1 g, 68 mmol) in acetic acid (80 mL) was warmed to 40° C. Tetramethyl-ammoniumbromide (0.105 g, 0.7 mmol) and activated zinc-powder (26.8 g, 410 mmol) was added in portions (2 g every 30 min) with stirring (argon atmosphere). The suspension was stirred for 16 h at 50° C. after which time another batch of activated zinc-powder (10 g, in 5 portions of 2 g each) was added. Stirring at 50° C. continued for another 3 h after which time the mixture was cooled to room temperature and poured into water (1000 mL). Concentrated NaOH solution (~150 mL) was added till pH 14 was attained. Ethyl acetate (500 mL) was added and the mixture stirred in the cold for 15 min. The suspension was filtered through Celite® and the filter cake thoroughly washed with ethyl acetate (5×300 mL). The filtrate was collected, phases were separated, the water phase was extracted once with ethyl acetate (500 mL), and organic phases were pooled and dried with Na$_2$SO$_4$. Solvents were evaporated and the brown, solid residue (21.1 g) was purified by chromatography on silica with ethyl acetate/n-heptane (2:1) to give the title compound as a off white solid (17.4 g, 80%), LC-MS (peak area/EIC) 100%, 318.1 (M+H)$^+$.

Example 10

6-(4-Chloro-phenyl)-5-(2,2,2-trifluoro-ethoxy)-pyridine-2-carboxylic acid {(S)-2-[(E)-methoxyimino]-cyclohexyl}-amide

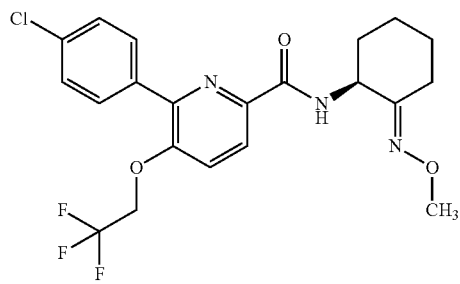

To a suspension of 0.110 g 6-(4-chloro-phenyl)-5-(2,2,2-trifluoro-ethoxy)-pyridine-2-carboxylic acid in 2 ml dichloromethane was added 0.052 g Ghosez's reagent ((1-chloro-2-methyl-propenyl)-dimethyl-amine) and the mixture was stirred at ambient temperature for 5 h. When a solution was obtained 0.065 g (S)-2-amino-cyclohexanone-(E)-O-methyl-oxime hydrochloride and 0.129 g Huenig's base (N,N-diisopropyl ethyl amine) were added and the mixture was stirred at ambient temperature for 30 min. The reaction mixture was quenched by addition of 10% aqueous citric acid. The phases were separated and the organic phase was purified by chromatography on silica gel with a gradient of heptane:ethyl acetate=9:1 to 1:1 to yield 0.060 g of the title compound as white solid. LC-MS (peak area/EIC) 100%, 456.1 (M+H)$^+$.

The starting material was prepared as follows:

Example 10b 6-(4-Chloro-phenyl)-5-(2,2,2-trifluoro-ethoxy)-pyridine-2-carboxylic acid

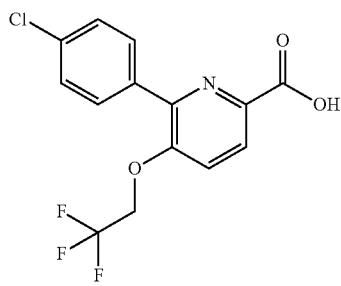 [SMILES: O=C(O)c1ccc(OCC(F)(F)F)c(-c2ccc(Cl)cc2)n1]

The title compound was obtained in analogy to the procedures detailed in Example 16 by substituting 6-chloro-4-(4-chloro-phenyl)-3-(2,2,2-trifluoro-ethoxy)-pyridazine with 6-chloro-2-(4-chloro-phenyl)-3-(2,2,2-trifluoro-ethoxy)-pyridine. MS (EI): 330.2 (M–H).

Example 10c

6-Chloro-2-(4-chloro-phenyl)-3-(2,2,2-trifluoro-ethoxy)-pyridine

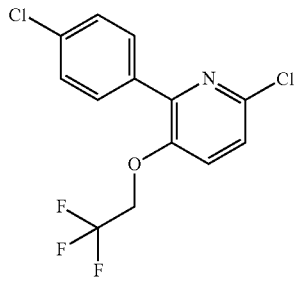 [SMILES: FC(F)(F)COc1ccc(Cl)nc1-c1ccc(Cl)cc1]

To a solution of 1.273 g trifluoroethanol in 20 ml dimethylsulfoxide was added 0.463 g sodiumhydride 55% in oil and the mixture was stirred at room temperature for 15 min. To the resulting solution was added a solution of 3.2 g 6-chloro-2-(4-chloro-phenyl)-3-fluoro-pyridine in 10 ml dimethylsulfoxide and the mixture was stirred at room temperature for 3 h. The reaction mixture was partitioned between water and ethyl acetate. The phases were separated and the organic phase was purified by chromatography on silica gel with a gradient of heptane to dichloromethane to yield 3.30 g of the title compound as slightly yellow solid. MS (EI): 322.1 and 324.2 (M+H). The product was obtained as 85:15 mixture of F vs Cl substitution products (6-chloro-2-(4-chloro-phenyl)-3-(2,2,2-trifluoro-ethoxy)-pyridine vs. 2-(4-chloro-phenyl)-3-fluoro-6-(2,2,2-trifluoro-ethoxy)-pyridine) that were better separable at the next step.

Example 10d

6-Chloro-2-(4-chloro-phenyl)-3-fluoro-pyridine

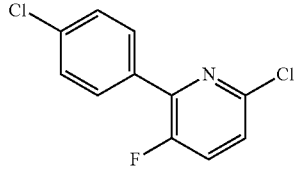 [SMILES: Fc1ccc(Cl)nc1-c1ccc(Cl)cc1]

A solution of 2.2 g 2,4-chloro-5-fluoropyridine, 2.28 g 4-chlorophenylboronic acid and 0.6 g tetrakistriphenylphosphine palladium in 30 ml tetrahydrofuran was added 30 ml of a 10% a solution of potassium carbonate in water and the mixture was stirred at ambient temperature for 18 h. The reaction mixture was diluted with ethyl acetate and water. The phases were separated and the organic phase was washed water, 10% aqueous citric acid, 10% aqueous sodium bicarbonate and brine, dried over sodium sulfate and evaporated. The residue was purified by chromatography on silica gel with a gradient of heptane:dichloromethane=9:1 to 1:1 (only startspot was removed) The product fractions were collected and evaporated. The residue was subjected to Kugelrohr distillation at 0.03 mbar and 110° C. to yield 1.72 g of the title compound as colorless oil which solidified into white crystals. MS (EI) (M+H): 241 and 243:

Example 11

N-(E)-(2-Cyclopropyl-2-hydroxyimino-ethyl)-5-(3,4-dichloro-phenyl)-6-(2,2,2-trifluoro-ethoxy)-nicotinamide

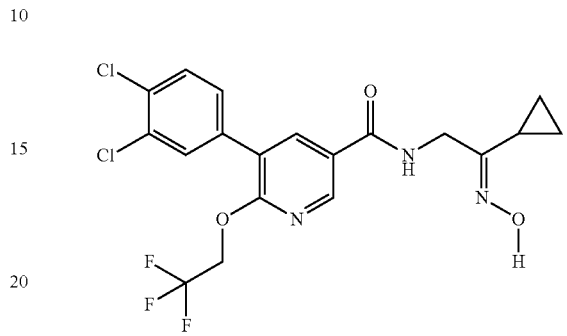

To a solution of 0.100 g N-(2-cyclopropyl-2-oxo-ethyl)-5-(3,4-dichloro-phenyl)-6-(2,2,2-trifluoro-ethoxy)-nicotinamide in 1.0 ml methanol was added 0.052 g of 50% aqueous hydroxylamine and the mixture was kept at ambient temperature for 18 h. The solvent was evaporated and the residue was purified by chromatography on silica gel with a gradient of heptane:ethyl acetate=9:1 to 1:1 to yield 0.093 g of the title compound as white crystals. MS (EI): 462.0599 (M+H).

The starting material was prepared as follows

Example 11b

N-(2-cyclopropyl-2-oxo-ethyl)-5-(3,4-dichloro-phenyl)-6-(2,2,2-trifluoro-ethoxy)-nicotinamide

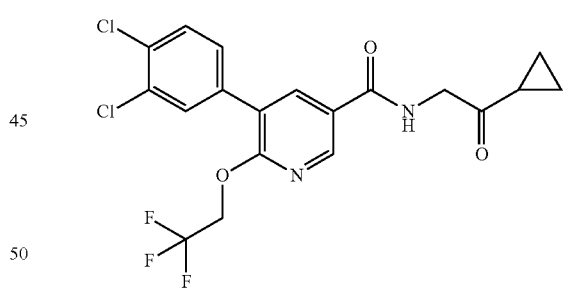

A solution of 0.080 g (2-cyclopropyl-2-oxo-ethyl)-carbamic acid tert-butyl ester in 1 ml trifluoroacetic acid was kept at room temperature for 30 min. The solvent was evaporated and to the resulting residue was added a solution of the acid chloride obtained from 0.140 g 5-(3,4-dichloro-phenyl)-6-(2,2,2-trifluoro-ethoxy)-nicotinic acid and 0.056 g Ghosez's reagent ((1-chloro-2-methyl-propenyl)-dimethyl-amine) in 2 ml dichloromethane by reaction at ambient temperature for 30 min. To the resulting mixture was added 0.15 g N,N-diisopropyl ethyl amine and the mixture was stirred at ambient temperature for 30 min. The reaction mixture was quenched by addition of 10% aqueous citric acid. The phases were separated and the organic phase was purified by chromatography on silica gel with a gradient of heptane:ethyl acetate=9:1 to 1:1 to yield 0.145 g of the title compound as colorless crystals. MS (EI): 447.0490 (M+H).

Example 11c (2-Cyclopropyl-2-oxo-ethyl)-carbamic acid tert-butyl ester

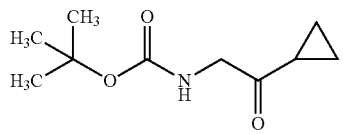

To 22 ml of a 0.5M solution of cyclopropylmagnesium bromide in tetrahydrofuran was added 2.2 g [(methoxy-methyl-carbamoyl)-methyl]-carbamic acid tert-butyl ester at −10° C. (acetone/ice) and the mixture was stirred at −10° C. for 30 min and then at ambient temperature for 30 min. (tlc shows little conversion heptanes:ethyl acetate=1:1) To the resulting colorless solution was added another 22 ml of a 0.5M solution of cyclopropylmagnesium bromide in tetrahydrofuran and the mixture was stirred at ambient temperature for 18 h. The reaction mixture was quenched by addition of 10% citric acid. The phases were separated and the organic phase was purified by chromatography on silica gel with a gradient of heptane:ethyl acetate=9:1 to 1:1 to yield 1.300 g of the title compound as colorless oil. MS (EI): 199 (M+).

Example 12

N-{2-Cyclopropyl-2-[(E)-methoxyimino]-ethyl}-5-(3,4-dichloro-phenyl)-6-(2,2,2-trifluoro-ethoxy)-nicotinamide

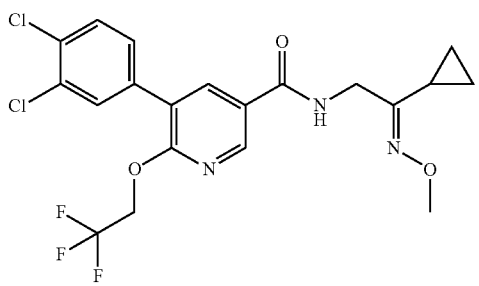 [SMILES: CO/N=C(/CNC(=O)c1cnc(OCC(F)(F)F)c(-c2ccc(Cl)c(Cl)c2)c1)C1CC1]

To a suspension of 0.183 g 5-(3,4-dichloro-phenyl)-6-(2,2,2-trifluoro-ethoxy)-nicotinic acid in 2 ml dichloromethane was added 0.073 g Ghosez's reagent ((1-chloro-2-methyl-propenyl)-dimethyl-amine) and the mixture was stirred at ambient temperature for 30 min. When a solution was obtained 0.082 g 2-cyclopropyl-2-[(E/Z)-methoxyimino]-ethyl-ammonium chloride and 0.193 g Huenig's base (N,N-diisopropyl ethyl amine) were added and the mixture was stirred at ambient temperature for 30 min. The reaction mixture was quenched by addition of 10% aqueous citric acid. The phases were separated and the organic phase was purified by chromatography on silica gel with a gradient of heptane: ethyl acetate=9:1 to 1:1 to yield 0.205 g of the title compound as crystals. This material was subjected to separation of geometrical isomers by chromatography on Chiralpack AD to yield 0.127 g of the title compound as light yellow gum. MS (EI): 476.0576 (M+H).

Examples 13 and 14

5-(4-Chloro-phenyl)-N-{2-cyclopropyl-2-[(Z)-methoxyimino]-ethyl}-6-(2,2,2-trifluoro-ethoxy)-nicotinamide and 5-(4-Chloro-phenyl)-N-{2-cyclopropyl-2-[(E)-methoxyimino]-ethyl}-6-(2,2,2-trifluoro-ethoxy)-nicotinamide

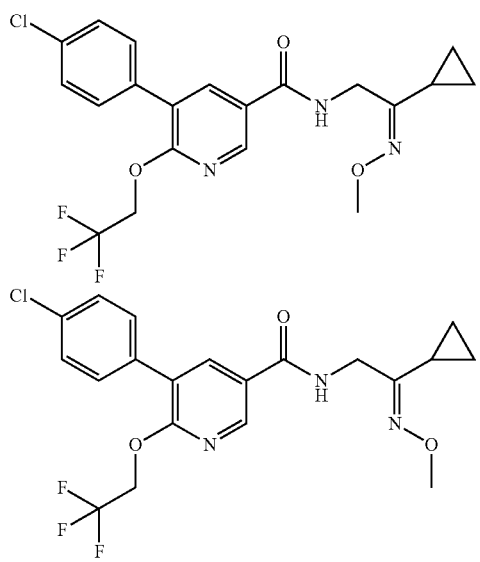

The title compounds were obtained as white solids in analogy to Example 12 by substituting 5-(3,4-dichloro-phenyl)-6-(2,2,2-trifluoro-ethoxy)-nicotinic acid with 5-(4-chloro-phenyl)-6-(2,2,2-trifluoro-ethoxy)-nicotinic acid. MS (EI): 476.0576 (M+H) with m.p. 125-128° C. and MS (EI): 476.0575 (M+H) with m.p. 100-102° C., respectively.

Example 15

5-(3,4-Dichloro-phenyl)-6-(2,2,2-trifluoro-ethoxy)-N-{3,3,3-trifluoro-2-[(Z)-methoxyimino]-propyl}-nicotinamide

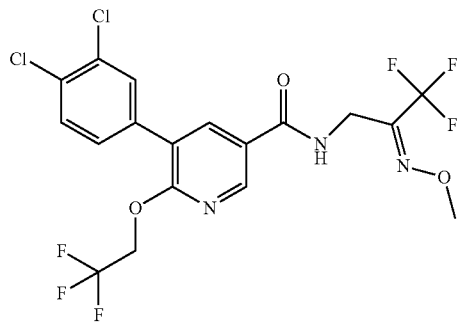 [SMILES: CO/N=C(/CNC(=O)c1cnc(OCC(F)(F)F)c(-c2ccc(Cl)c(Cl)c2)c1)C(F)(F)F]

To a solution of 0.241 g 5-(3,4-dichloro-phenyl)-6-(2,2,2-trifluoro-ethoxy)-N-(3,3,3-trifluoro-2-oxo-propyl)-nicotinamide in ethanol was added 0.051 g O-methylhydroxylamine hydrochloride and the mixture was kept at ambient temperature for 18 h. The mixture was then heated to reflux for 4 h. The clear reaction mixture was diluted with ca 2 ml water and concentrated under aspirator vacuum whereby crystallisation occurred. The product was collected by filtration and washed with water and dried to constant weight under high vacuum to yield 0.23 g of the title compound as white crystals melting at 124-126° C. MS (EI): 502.1 (M−H).

The starting materials were prepared as follows:

Example 15b 5-(3,4-Dichloro-phenyl)-6-(2,2,2-trifluoro-ethoxy)-N-(3,3,3-trifluoro-2-oxo-propyl)-nicotinamide

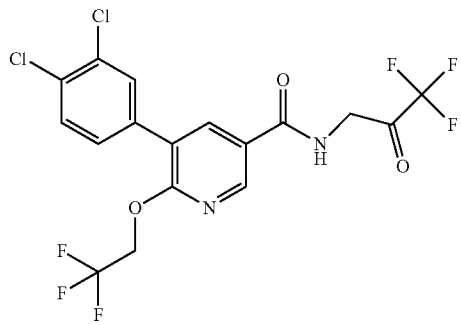 [SMILES: O=C(NCC(=O)C(F)(F)F)c1cnc(OCC(F)(F)F)c(-c2ccc(Cl)c(Cl)c2)c1]

A suspension of 3.00 g 2-[5-(3,4-dichloro-phenyl)-6-(2,2,2-trifluoro-ethoxy)-pyridin-3-yl]-4-(2,2,2-trifluoro-acetyl)-4H-oxazol-5-one in 15 ml water and 15 ml dioxan was heated to reflux for 1 h. The resulting slightly turbid solution was partitioned between water and ethyl acetate. The phases were separated and the organic phase was purified by chromatography on silica gel with heptane:ethyl acetate=9:1 to 1:1. The product fractions were concentrated and the residue was taken up in dichloromethane whereby crystallization occurred. The solid was collected by filtration and washed with little dichloromethane to yield 1.60 g of the title compound as white solid. m.p.: 122-124° C. MS (EI): 474 (M+).

Example 15c

2-[5-(3,4-Dichloro-phenyl)-6-(2,2,2-trifluoro-ethoxy)-pyridin-3-yl]-4-(2,2,2-trifluoro-acetyl)-4H-oxazol-5-one

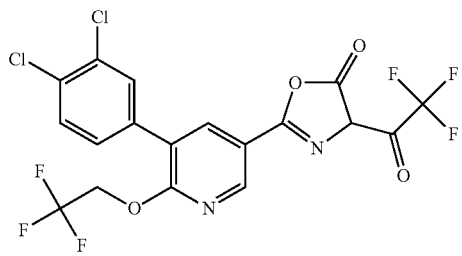 [SMILES: O=C1OC(c2cnc(OCC(F)(F)F)c(-c3ccc(Cl)c(Cl)c3)c2)=NC1C(=O)C(F)(F)F]

To a solution of 3.00 g {[5-(3,4-dichloro-phenyl)-6-(2,2,2-trifluoro-ethoxy)-pyridine-3-carbonyl]-amino}-acetic acid in 30 ml acetone was added drop wise at 0° C. 4.467 g trifluoroacetic acid anhydride and the mixture was stirred with warming to room temperature for 18 h. The solvents were evaporated and the residue was dried under high vacuum. The resulting yellow gum was triturated under water and a little methanol and the mixture was stirred (ca 1 h) until homogenous slurry was obtained. The solid was collected by filtration and dried to constant weight under high vacuum to yield 3.46 g of the title compound as pale yellow powder. MS (EI): 501.0 (M+H).

Example 15d

{[5-(3,4-dichloro-phenyl)-6-(2,2,2-trifluoro-ethoxy)-pyridine-3-carbonyl]-amino}-acetic acid

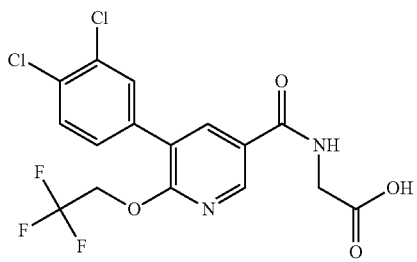 [SMILES: O=C(O)CNC(=O)c1cnc(OCC(F)(F)F)c(-c2ccc(Cl)c(Cl)c2)c1]

A solution of 4.00 g {[5-(3,4-dichloro-phenyl)-6-(2,2,2-trifluoro-ethoxy)-pyridine-3-carbonyl]-amino}-acetic acid tert-butyl ester in 20 ml trifluoroacetic acid was kept at ambient temperature for 30 min. The solvent was evaporated and the residue was dried under high vacuum. The residue was taken up in toluene and the solvent was evaporated to leave a semi solid residue. The residue was taken up in toluene and dichloromethane and the solvents were evaporated to leave a crystalline residue which was taken up in heptane and ethyl acetate and stirred until homogenous slurry was obtained. The solid was collected by filtration, washed with heptane and dried to constant weight to yield 3.47 g of the title compound as white crystalline powder. MS (EI): 422 (M+).

Example 15e

{[5-(3,4-Dichloro-phenyl)-6-(2,2,2-trifluoro-ethoxy)-pyridine-3-carbonyl]-amino}-acetic acid tert-butyl ester

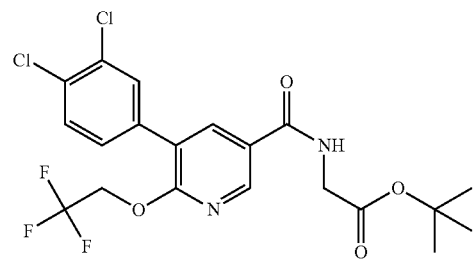 [SMILES: CC(C)(C)OC(=O)CNC(=O)c1cnc(OCC(F)(F)F)c(-c2ccc(Cl)c(Cl)c2)c1]

To a suspension of 3.66 g 5-(3,4-dichloro-phenyl)-6-(2,2,2-trifluoro-ethoxy)-nicotinic acid in 40 ml dichloromethane was added 1.469 g Ghosez's reagent ((1-chloro-2-methyl-propenyl)-dimethyl-amine)) and the mixture was stirred at ambient temperature for 30 min. To the resulting solution was added 3.224 g N,N-diisopropylethylamine and 1.44 g glycine-t-butylester and the mixture was stirred at ambient temperature for 30 min. The reaction mixture was quenched by addition of 10% aqueous citric acid. The phases were separated and the organic phase was purified by chromatography on silica gel with heptane:ethyl acetate=9:1 to 1:1 to yield 4.10 g of the title compound as white foam. MS (EI): 477.0608 (M−H).

Example 15f 5-(3,4-Dichloro-phenyl)-6-(2,2,2-trifluoro-ethoxy)-nicotinic acid

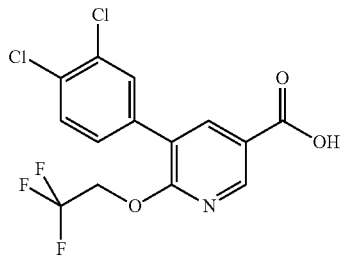 [SMILES: O=C(O)c1cnc(OCC(F)(F)F)c(-c2ccc(Cl)c(Cl)c2)c1]

In analogy to 5-(4-chloro-phenyl)-6-(2,2,2-trifluoro-ethoxy)-nicotinic acid (WO 2008/040651) by substituting 4-chlorophenylboronic acid with 3,4-dichlorophenylboronic acid the title compound was obtained as white solid. MS (EI): 365.9 and 364.1 (M−H).

Example 16

5-(4-Chloro-phenyl)-6-(2,2,2-trifluoro-ethoxy)-pyridazine-3-carboxylic acid {(R)-2-[(E)-methoxy-imino]-cyclohexyl}-amide

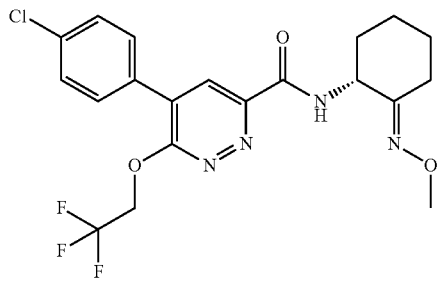 [SMILES: CO/N=C1\CCCC[C@H]1NC(=O)c1cc(-c2ccc(Cl)cc2)c(OCC(F)(F)F)nn1]

To a solution of 100 mg of 5-(4-chloro-phenyl)-6-(2,2,2-trifluoro-ethoxy)-pyridazine-3-carboxylic acid ((R)-2-oxo-cyclohexyl)-amide in 0.5 ml methanol and 0.5 ml water, was added 98 mg O-methylhydroxylamine hydrochloride and the mixture was stirred at ambient temperature for 3.5 h. The solvents were evaporated and the residue was purified by chromatography on silica gel using a gradient of heptane:ethyl acetate=95:5 to 50:50 to yield 91 mg of the title compound as white foam. MS (EI): 457.3 (M+H).

The starting materials were prepared as follows:

Example 16b 5-(4-Chloro-phenyl)-6-(2,2,2-trifluoro-ethoxy)-pyridazine-3-carboxylic acid ((R)-2-oxo-cyclohexyl)-amide

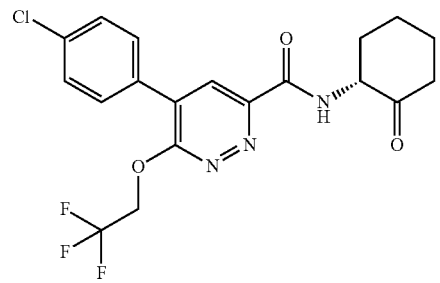 [SMILES: O=C(N[C@@H]1CCCCC1=O)c1cc(-c2ccc(Cl)cc2)c(OCC(F)(F)F)nn1]

In analogy to Example 1b by substituting 5-(3,4-dichloro-phenyl)-N-((1S,2R)-2-hydroxy-cyclohexyl)-6-(2,2,2-trifluoro-ethoxy)-nicotinamide with 5-(4-chloro-phenyl)-6-(2,2,2-trifluoro-ethoxy)-pyridazine-3-carboxylic acid ((1R,2R)-2-hydroxy-cyclohexyl)-amide the title compound was obtained as white foam. MS (EI): 430.3 (M+H).

Example 16c 5-(4-Chloro-phenyl)-6-(2,2,2-trifluoro-ethoxy)-pyridazine-3-carboxylic acid ((1R,2R)-2-hydroxy-cyclohexyl)-amide

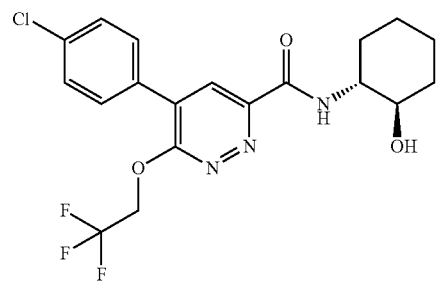 [SMILES: O=C(N[C@@H]1CCCC[C@H]1O)c1cc(-c2ccc(Cl)cc2)c(OCC(F)(F)F)nn1]

To a suspension of 0.300 mg 5-(4-chloro-phenyl)-6-(2,2,2-trifluoro-ethoxy)-pyridazine-3-carboxylic acid in 1 ml dichloromethane was added 0.137 mL 1-chloro-N,N,2-trimethyl-propenylamine and the mixture was stirred at ambient temperature for 30 min. The resulting slightly yellow solution was added to a solution of 130 mg (1R,2R)-2-amino-cyclohexanol and 0.224 ml N,N-diisopropylethylamine in 3 ml dimethylformamide and the mixture was stirred at ambient temperature for 3 h. The reaction mixture was partitioned between 10% aqueous citric acid and ethyl acetate. The phases were separated and the organic phase was purified by chromatography on silica gel using a gradient of heptane:

ethyl acetate of 95:5 to 50:50 to yield 324 mg of the title compound as white solid. MS (EI): 430.3 (M+H).

Example 16d 5-(4-chloro-phenyl)-6-(2,2,2-trifluoro-ethoxy)-pyridazine-3-carboxylic acid

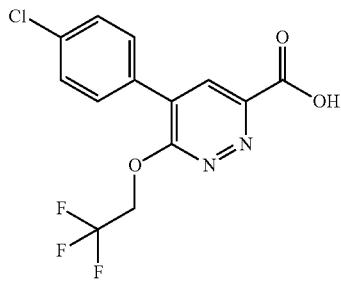 [SMILES: O=C(O)c1cc(-c2ccc(Cl)cc2)c(OCC(F)(F)F)nn1]

To a solution of 0.865 g 5-(4-chloro-phenyl)-6-(2,2,2-trifluoro-ethoxy)-pyridazine-3-carboxylic acid methyl ester in 9.0 ml tetrahydrofurane was added 3.2 ml of a 1M of lithium hydroxide in water was added and the mixture was stirred at ambient temperature for 3 h. The reaction mixture was acidified with 1 M hydrochloric acid. The solid was collected by filtration washed with water and dried under high vacuum to yield 0.805 g of the title compound as white solid, MS (EI): 331.1 (M−H).

Example 16e 5-(4-chloro-phenyl)-6-(2,2,2-trifluoro-ethoxy)-pyridazine-3-carboxylic acid methyl ester

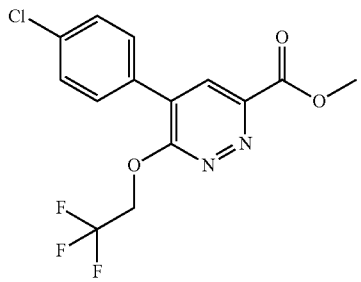 [SMILES: COC(=O)c1cc(-c2ccc(Cl)cc2)c(OCC(F)(F)F)nn1]

To a solution of 0.882 g 6-chloro-4-(4-chloro-phenyl)-3-(2,2,2-trifluoro-ethoxy)-pyridazine in methanol was added 0.626 g triethylamine and 0.081 g PdCl$_2$. dppf. CH$_2$Cl$_2$. The mixture was heated to 110° C. under an atmosphere of 70 bar carbon monoxide for 20 h. The reaction mixture was cooled to room temperature. The solids were removed by filtration and the mother liquor was evaporated and purified by chromatography on silica gel using a gradient of heptane:ethyl acetate of 95:5 to 50:50 to yield 0.870 g of the title compound as white solid MS (EI): 347.1 (M+H).

Example 16f

6-Chloro-4-(4-chloro-phenyl)-3-(2,2,2-trifluoro-ethoxy)-pyridazine

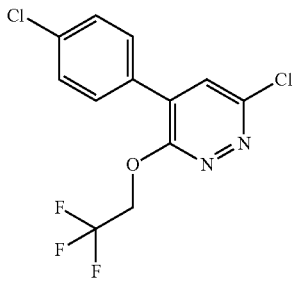 [SMILES: FC(F)(F)COc1nnc(Cl)cc1-c1ccc(Cl)cc1]

A mixture of 0.676 g 4-bromo-6-chloro-3-(2,2,2-trifluoro-ethoxy)-pyridazine, 363 mg 4-chlorophenylboronic acid, 641 mg potassium carbonate and 134 mg tetrakis(triphenylphosphine) palladium in 15 ml tetrahydrofuran and 15 ml water was heated to reflux for 18 h. The reaction mixture was partitioned between water and ethyl acetate. The phases were separated and the organic phase was purified by chromatography on silica gel using a gradient of heptane:ethyl acetate of 95:5 to 50:50 to yield 0.493 g of the title compound as white solid. MS (EI): 323.1 (M+H).

Example 16g

4-Bromo-6-chloro-3-(2,2,2-trifluoro-ethoxy)-pyridazine

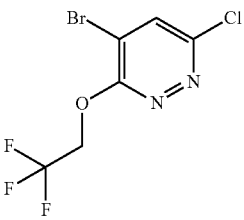 [SMILES: FC(F)(F)COc1nnc(Cl)cc1Br]

To a suspension of 2.30 g 6-chloro-3-(2,2,2-trifluoro-ethoxy)-pyridazin-4-ylamine in 23 ml dibromomethane was added 5.11 g isoamylnitrite at once and drop wise 4.642 g trimethylbromosilane at ambient temperature (during ca. 10 min). A moderate exotherm reaction was observed and a dark brown solution was obtained. The mixture was stirred at ambient temperature for 18 h. The solvents were evaporated and the residue was purified (3 times) by chromatography on silica gel using a gradient of heptane to dichloromethane to yield 0.70 g the title compound as white crystalline solid. MS (EI): 292 (M+H).

Example 16h

6-Chloro-3-(2,2,2-trifluoro-ethoxy)-pyridazin-4-ylamine

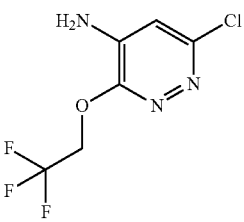 [SMILES: Nc1cc(Cl)nnc1OCC(F)(F)F]

To a solution of 3.28 g 3,6-dichloro-pyridazin-4-ylamine in 30 ml dimethylsulfoxide and 4.0 g trifluoroethanol was added 1.84 g lithium hydroxide hydrate and 3 ml water and the mixture was heated to 80° C. for 18 h. The reaction mixture was diluted with 100 ml water and stirred at ambient temperature for 2 h. The resulting solid was collected by filtration washed with water and dried to constant weight under high vacuum to yield 3.84 g of the title compound as off white crystals. MS (EI): 228.1 and 230.1 (M+H).

Example 17

5-(4-Chloro-phenyl)-6-(2,2,2-trifluoro-ethoxy)-pyridazine-3-carboxylic acid {(S)-2-[(E)-methoxy-imino]-cyclohexyl}-amide

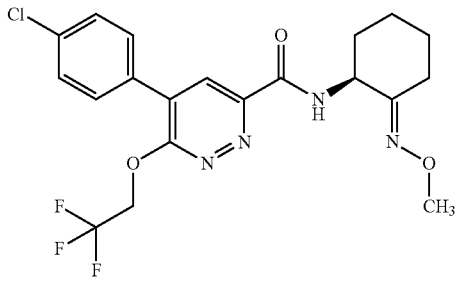

In analogy to Example 16 by substituting (1R,2R)-2-amino-cyclohexanol (Example 16c) with (1R,2S)-2-amino-cyclohexanol the title compound was obtained as white foam. MS (EI): 457.3 (M+H).

Example 18

5-(4-Chloro-phenyl)-6-cyclopropylmethoxy-pyridazine-3-carboxylic acid {(S)-2-[(E)-methoxy-imino]-cyclohexyl}-amide

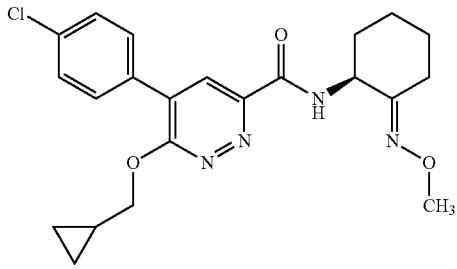

In analogy to Example 9 by substituting 4-(4-chloro-phenyl)-5-(2,2,2-trifluoro-ethoxy)-pyridine-2-carboxylic with 5-(4-chloro-phenyl)-6-cyclopropylmethoxy-pyridazine-3-carboxylic acid the title compound was obtained as white foam. MS (EI): 429.2 (M+H).

The starting material was prepared as follows:

Example 18b 5-(4-Chloro-phenyl)-6-cyclopropylmethoxy-pyridazine-3-carboxylic acid

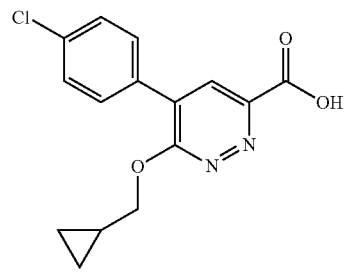 [SMILES: O=C(O)c1cc(-c2ccc(Cl)cc2)c(OCC2CC2)nn1]

In analogy to Example 16d-f by substituting 4-bromo-6-chloro-3-(2,2,2-trifluoro-ethoxy)-pyridazine with 6-chloro-3-cyclopropylmethoxy-4-iodo-pyridazine the title compound was obtained as white solid. MS (EI): 303.1 (M–H).

Example 18c

6-Chloro-3-cyclopropylmethoxy-4-iodo-pyridazine

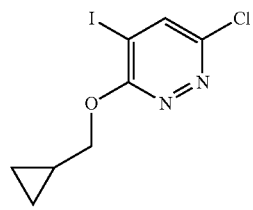 [SMILES: Clc1cc(I)c(OCC2CC2)nn1]

To a solution of 0.988 ml 2,2,6,6-tetramethylpiperidine in 10 ml tetrahydrofurane was added 3.534 ml of a 1.6M solution of n-butyl lithium in hexane at ambient temperature and the mixture was stirred at room temperature for 30 min. To this solution was added rapidly a precooled (−75° C.) solution of 0.300 g 3-chloro-6-cyclopropylmethoxy-pyridazine in 10 ml tetrahydrofuran at −75° C. After 5 minutes, a precooled solution of 0.701 g iodine in 10 ml THF was added rapidly. The reaction mixture was stirred at −75° C. for 30 minutes and then quenched with a saturated aqueous solution of ammonium chloride and diluted with ethyl acetate. The phases were separated and the organic phase was purified by chromatography on silica gel using a gradient of heptane:ethyl acetate=95:5 to 50:50 to yield 0.206 g of the title compound as light yellow solid. MS (EI): 310.9 (M+H).

Example 18d

3-Chloro-6-cyclopropylmethoxy-pyridazine

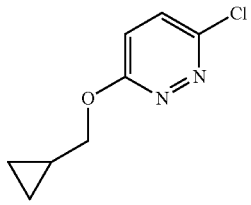 [SMILES: Clc1ccc(OCC2CC2)nn1]

To a solution of 1.016 ml cyclopropanemethanol in 10 ml dimethylsulfoxide was added 0.564 g sodium hydride 55% in mineral oil and the mixture was stirred at room temperature for 15 min. The resulting solution was added drop wise to a solution of 2.0 g 3,6-dichloropyridazine in 20 ml dry dimethylsulfoxide at room temperature and stirred at this temperature for 1 h. The reaction mixture was partitioned between water and ethyl acetate, the phases were separated and the organic phase was purified by chromatography on silica gel using a gradient of heptane: ethyl acetate=95:5 to 40:60 to yield 1.88 g of the title compound as white solid. MS (EI): 185.05 (M+H).

Examples 19 and 20

4-(4-Chloro-phenyl)-5-cyclopropylmethoxy-pyrimidine-2-carboxylic acid {2-cyclopropyl-2-[(Z)-methoxyimino]-ethyl}-amide and 4-(4-chloro-phenyl)-5-cyclopropylmethoxy-pyrimidine-2-carboxylic acid {2-cyclopropyl-2-[(E)-methoxyimino]-ethyl}-amide

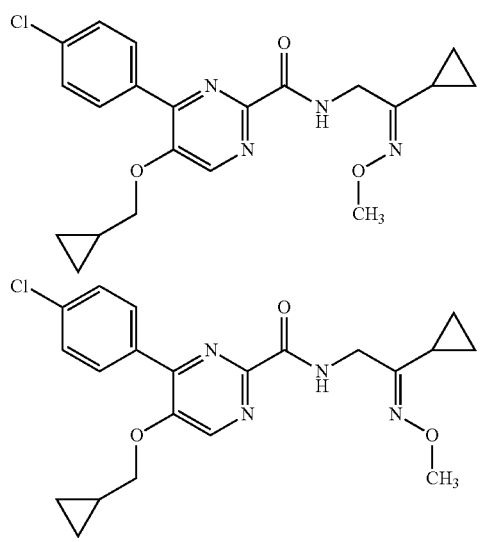

The title compounds were obtained in analogy to Example 12 by substituting 5-(3,4-dichloro-phenyl)-6-(2,2,2-trifluoro-ethoxy)-nicotinic acid with 4-(4-chloro-phenyl)-5-cyclopropylmethoxy-pyrimidine-2-carboxylic acid as white solids. MS (EI): 414.1 (M+H) with m.p.: 135-140° C. and MS (EI): 414.1 (M+H) with m.p.: 146-150° C., respectively).

The starting material was prepared as follows:

Example 19b 4-(4-Chloro-phenyl)-5-cyclopropylmethoxy-pyrimidine-2-carboxylic acid

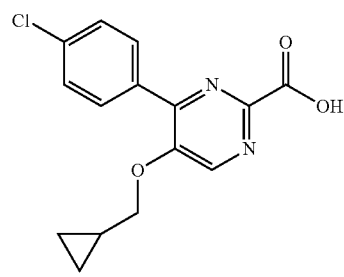 [SMILES: O=C(O)c1ncc(OCC2CC2)c(-c2ccc(Cl)cc2)n1]

To a solution of 2.655 g 4-(4-chloro-phenyl)-5-cyclopropylmethoxy-pyrimidine-2-carboxylic acid methyl ester in 27 ml tetrahydrofuran was added 11 ml of a 1M solution of lithium hydroxide in water and the mixture was stirred at room temperature for 1 h. The reaction mixture was acidified by addition of 1M hydrochloric acid. The precipitate was collected by filtration, washed with water and dried to constant weight under high vacuum to yield 2.473 g of the title compound as white solid. MS (EI): 305.1 (M+H).

Example 19c 4-(4-chloro-phenyl)-5-cyclopropylmethoxy-pyrimidine-2-carboxylic acid methyl ester

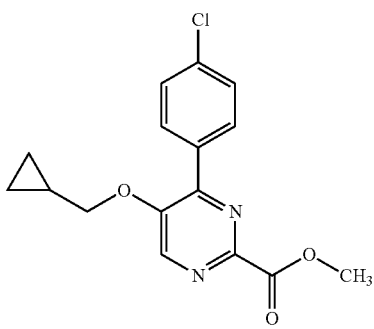 [SMILES: COC(=O)c1ncc(OCC2CC2)c(-c2ccc(Cl)cc2)n1]

In analogy to Example 16e by substituting 6-chloro-4-(4-chloro-phenyl)-3-(2,2,2-trifluoro-ethoxy)-pyridazine with 2-chloro-4-(4-chloro-phenyl)-5-cyclopropylmethoxy-pyrimidine the title compound was obtained as white solid. MS (EI): 319.2 (M+H).

Example 19d

2-Chloro-4-(4-chloro-phenyl)-5-cyclopropyl-methoxy-pyrimidine

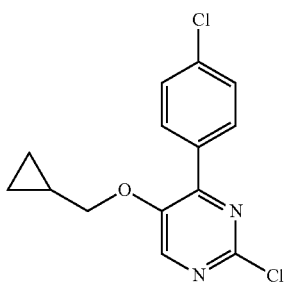 [SMILES: Clc1ccc(-c2nc(Cl)ncc2OCC2CC2)cc1]

To a solution of 0.948 ml cyclopropanemethanol in 13 ml dimethylformamide was added 0.468 g sodium hydride 55% in mineral oil and the reaction mixture was stirred at room temperature for 15 min. The resulting solution was added drop wise to a solution of 2.586 g 2-chloro-4-(4-chloro-phenyl)-5-fluoro-pyrimidine at 0° C. and the mixture was stirred at 0° C. for 30 min. The reaction mixture was partitioned between water and ethyl acetate. The phases were separated and the organic phase was purified by chromatography on silica gel using a gradient of heptane:ethyl acetate=10:90 to 80:20 to yield 2.50 g of the title compound as white solid. MS (EI): 295.2 (M+H).

Example 19e

2-Chloro-4-(4-chloro-phenyl)-5-fluoro-pyrimidine

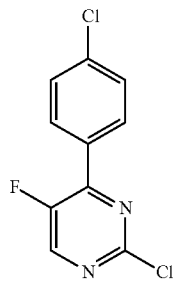 [SMILES: Fc1cnc(Cl)nc1-c1ccc(Cl)cc1]

A mixture of 5.00 g 2,4-dichloro-5-fluoropyrimidine, 4.683 g p-chlorophenylboronic acid, 1.730 g tetrakistriphenylphosphino palladium and 8.278 g potassium carbonate in 125 ml tetrahydrofurane and 125 ml water was heated to reflux for 3 h. The reaction mixture was cooled to room temperature and diluted with ethyl acetate. The phases were separated and the organic phase was washed with brine dried over sodium sulfate and evaporated. The solid residue was triturated in ca 60 ml methanol for 30 min. The solids were collected by filtration to yield 5.2 g of an off white solid (contains some boronic acid which gives a start spot). The mother liquor was evaporated and the residue was purified by chromatography on silica gel with heptane:ethyl acetate=8:2 to 1:1 to yield 1.0 g of the product as white solid. Both crops were combined and dissolved in ca 50 ml dichloromethane and filtered over ca 50 g silica gel with dichloromethane to remove a polar start spot. The filtrate was concentrated under aspirator vacuum whereby precipitation occurred. The solid was collected by filtration to yield 5.76 g of the title compound as white crystals. MS (EI): 230.1 and 228.1 (M+H).

Example 21

6-(4-Chloro-phenyl)-5-(2,2,2-trifluoro-ethoxy)-pyridine-2-carboxylic acid {3,3,3-trifluoro-2-[(Z)-methoxyimino]-propyl}-amide

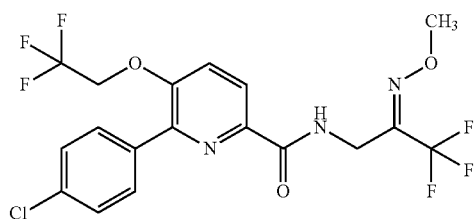 [SMILES: CO/N=C(/CNC(=O)c1ccc(OCC(F)(F)F)c(-c2ccc(Cl)cc2)n1)C(F)(F)F]

The title compound was obtained as white solid in analogy to Example 9 by substituting 4-(4-chloro-phenyl)-5-(2,2,2-trifluoro-ethoxy)-pyridine-2-carboxylic acid with 6-(4-chloro-phenyl)-5-(2,2,2-trifluoro-ethoxy)-pyridine-2-carboxylic acid and (S)-2-amino-cyclohexanone (E)-O-methyl-oxime hydrochloride with 3-amino-1,1,1-trifluoro-propan-2-one (Z)-O-methyl-oxime. MS (EI): 470.071 (M+H)

Example 22

N-{2-Cyclopropyl-2-[(E/Z)-2,2,2-trifluoro-ethoxyimino]-ethyl}-5-(3,4-dichloro-phenyl)-6-(2,2,2-trifluoro-ethoxy)-nicotinamide

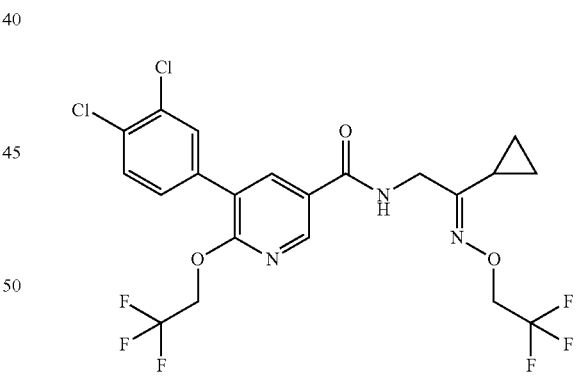

To a solution of 0.090 g N-(E)-(2-cyclopropyl-2-hydroxyimino-ethyl)-5-(3,4-dichloro-phenyl)-6-(2,2,2-trifluoroethoxy)-nicotinamide in 1 ml DMF 0.010 g sodium hydride was added and the reaction mixture was stirred for 30 minutes at room temperature. To the resulting solution 30 μl 2,2,2-trifluoroethyl trifluoromethanesulfonate was added and the reaction mixture was stirred at room temperature for 30 minutes. The reaction mixture was partitioned between water and ethyl acetate, the phases were separated and the organic phase was purified by chromatography on reversed phase U-0857 to yield 0.030 g of the title compound as colorless gum, mixture E/Z-oxime: 43/57. MS (EI): 544.0 (M+H).

Example 23

(E)-N-(2-cyclopropyl-2-(methoxyimino)ethyl)-5-(3,4-dichlorophenyl)-6-(2,2,2-trifluoroethoxy)pyridazine-3-carboxamide

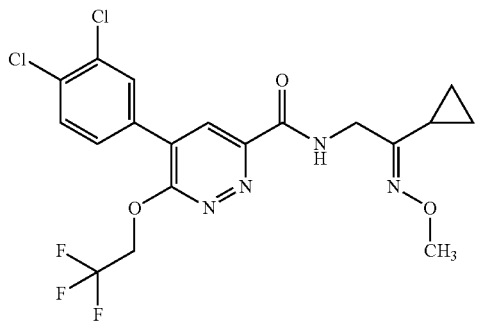 [SMILES: CO/N=C(/CNC(=O)c1cc(-c2ccc(Cl)c(Cl)c2)c(OCC(F)(F)F)nn1)C1CC1]

The title compound was obtained as white crystals (m.p.: 147-150° C.) in analogy to Example 12 by substituting 5-(3,4-dichloro-phenyl)-6-(2,2,2-trifluoro-ethoxy)-nicotinic acid with 5-(3,4-dichloro-phenyl)-6-(2,2,2-trifluoro-ethoxy)-pyridazine-3-carboxylic acid. MS (EI): 477.1 (M+H).

The starting material was obtained as follows:

Example 23b (3,4-dichloro-phenyl)-6-(2,2,2-trifluoro-ethoxy)-pyridazine-3-carboxylic acid

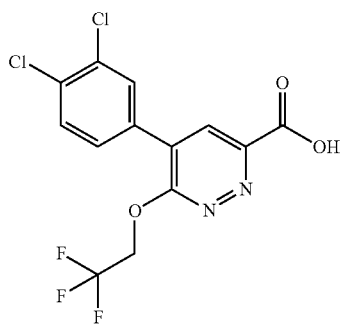 [SMILES: O=C(O)c1cc(-c2ccc(Cl)c(Cl)c2)c(OCC(F)(F)F)nn1]

The starting material (3,4-dichloro-phenyl)-6-(2,2,2-trifluoro-ethoxy)-pyridazine-3-carboxylic acid was obtained in analogy to the preparations described in Examples 16d-f by substituting 4-chlorophenylboronic acid with 3,4-dichlorophenylboronic acid. MS (EI): 365.1 (M−H).

Example 24

5-(3,4-Dichloro-phenyl)-6-(2,2,2-trifluoro-ethoxy)-pyridazine-3-carboxylic acid {(S)-2-[(E)-methoxyimino]-cyclohexyl}-amide

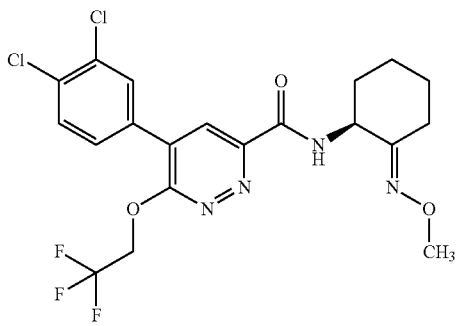 [SMILES: CO/N=C1\CCCC[C@@H]1NC(=O)c1cc(-c2ccc(Cl)c(Cl)c2)c(OCC(F)(F)F)nn1]

The title compound was obtained as white crystals (m.p.: 106-109° C.) in analogy to Example 10 by substituting 6-(4-chloro-phenyl)-5-(2,2,2-trifluoro-ethoxy)-pyridine-2-carboxylic acid with (3,4-dichloro-phenyl)-6-(2,2,2-trifluoro-ethoxy)-pyridazine-3-carboxylic acid. MS (EI): 491.1 (M−H).

Example 25

(S,E)-5-(4-Chlorophenyl)-N-(2-cyclopropyl-2-(methoxyimino)ethyl)-6-(1,1,1-trifluoropropan-2-yloxy)pyridazine-3-carboxamide

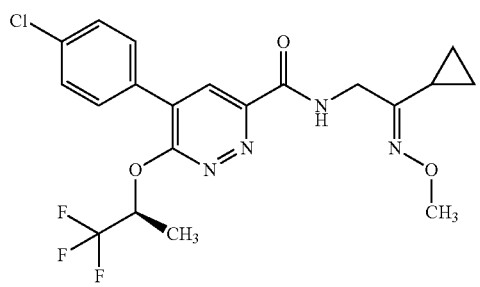 [SMILES: CO/N=C(/CNC(=O)c1cc(-c2ccc(Cl)cc2)c(O[C@@H](C)C(F)(F)F)nn1)C1CC1]

The title compound was obtained as white crystals (m.p.: 90-94° C.) in analogy to Example 23 by substituting (3,4-dichloro-phenyl)-6-(2,2,2-trifluoro-ethoxy)-pyridazine-3-carboxylic with 5-(4-chloro-phenyl)-6-(S)-2,2,2-trifluoro-1-methyl-ethoxy)-pyridazine-3-carboxylic acid. MS (EI): 345.1 (M−H).

The starting material was obtained as follows:

Example 25b 5-(4-Chloro-phenyl)-6-((S)-2,2,2-trifluoro-1-methyl-ethoxy)-pyridazine-3-carboxylic acid

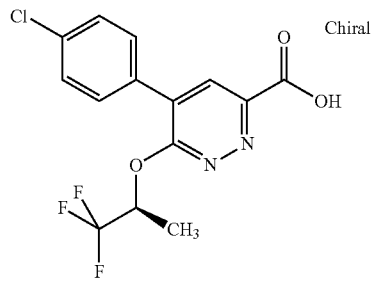 [SMILES: C[C@H](Oc1nnc(C(=O)O)cc1-c1ccc(Cl)cc1)C(F)(F)F]

The starting material 5-(4-chloro-phenyl)-6-((S)-2,2,2-trifluoro-1-methyl-ethoxy)-pyridazine-3-carboxylic acid was obtained in analogy to the preparations described in Examples 16d-h by substituting trifluoroethanol in Example 16h with (S)-1,1,1-trifluoro-propan-2-ol. MS (EI): 365.1 (M−H).

Example 26

(S,E)-6-(4-Chlorophenyl)-N-(2-cyclopropyl-2-(methoxyimino)ethyl)-5-(1,1,1-trifluoropropan-2-yloxy)pyrazine-2-carboxamide

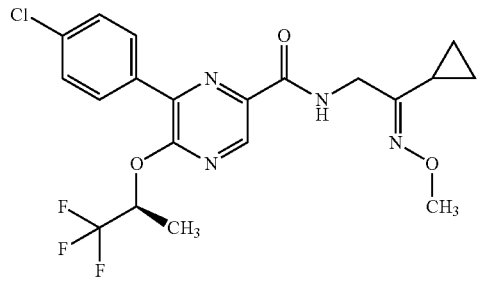 [SMILES: CO/N=C(/CNC(=O)c1cnc(O[C@@H](C)C(F)(F)F)c(-c2ccc(Cl)cc2)n1)C1CC1]

To a suspension of (S)-6-(4-chlorophenyl)-5-(1,1,1-trifluoropropan-2-yloxy)-pyrazine-2-carboxylic acid (0.2 g, 577 µmol, Eq: 1.00) in dimethylformamide (4 ml) were added under argon TBTU (204 mg, 635 µmol, Eq: 1.1), ethyldiisopropylamine (373 mg, 478 µl, 2.88 mmol, Eq: 5) and (E)-2-amino-1-cyclopropylethanone O-methyl oxime hydrochloride (104 mg, 635 µmol, Eq: 1.1) and the mixture was stirred at room temperature for 18 h overnight. The reaction mixture was partitioned between ethyl acetate and 10% aqueous citric acid, the phases were separated and the organic phase was dried over MgSO₄; filtered; concentrated and purified by flash chromatography (silica gel, 20 g, 5% to 50% ethyl acetate in heptane) to yield the title compound as white crystals (0.12 g, 45.5%, m.p.: 149-152° C.). MS (EI): 457.1 (M+H).

The starting materials were obtained as follows:

Example 26b (S)-6-(4-Chlorophenyl)-5-(1,1,1-trifluoropropan-2-yloxy)pyrazine-2-carboxylic acid The starting material (S)-6-(4-chlorophenyl)-5-(1,1,1-trifluoropropan-2-yloxy)pyrazine-2-carboxylic acid was obtained as follows

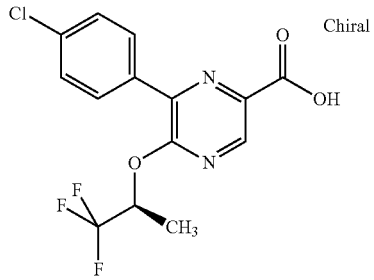 [SMILES: C[C@H](Oc1ncc(C(=O)O)nc1-c1ccc(Cl)cc1)C(F)(F)F]

To a suspension of (S)-methyl 6-(4-chlorophenyl)-5-(1,1,1-trifluoropropan-2-yloxy)pyrazine-2-carboxylate (0.72 g, 2.00 mmol, Eq: 1.00) in tetrahydrofurane (7 ml) was added a 1M LiOH solution in water (2.59 ml, 2.59 mmol, Eq: 1.3) and the reaction mixture was stirred at room temperature for 1 hour. The mixture was concentrated to remove tetrahydrofurane and diluted with water; acidified with 1M hydrochloric acid to pH 2 and extracted with ethyl acetate. The organic phase was dried with MgSO₄; filtered, evaporated and dried to constant weight under high vacuum to yield the title compound as white solid (0.70 g, 100%). MS (EI): 345.0 (M–H).

Example 26c (S)-Methyl 6-(4-chlorophenyl)-5-(1,1,1-trifluoropropan-2-yloxy)pyrazine-2-carboxylate

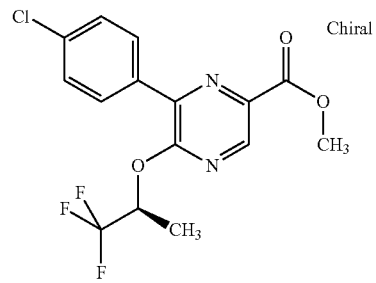 [SMILES: COC(=O)c1cnc(O[C@@H](C)C(F)(F)F)c(-c2ccc(Cl)cc2)n1]

To a solution of methyl 5-bromo-6-(4-chlorophenyl)pyrazine-2-carboxylate (0.847 g, 2.59 mmol, Eq: 1.00) in dry DMSO (8 ml) was added cesium carbonate (1.54 g, 2.84 mmol, Eq: 1.1) and (S)-1,1,1-trifluoro-2-propanol (324 mg, 233 µl, 2.84 mmol, Eq: 1.1) and the reaction mixture was stirred at room temperature for 3 hours. The reaction mixture was partitioned between water and ethyl acetate, the phases were separated and the organic phase was dried over MgSO4 evaporated and purified by flash chromatography (silica gel, 100 g, 10% to 50% ethyl acetate in heptane) to yield the title compound as light yellow oil (0.724 g, 77.6%). MS (EI): 361.1 (M+H).

Example 27

6-(4-Chlorophenyl)-N-((S,E)-2-(methoxyimino)cyclohexyl)-5-((S)-1,1,1-trifluoropropan-2-yloxy)pyrazine-2-carboxamide

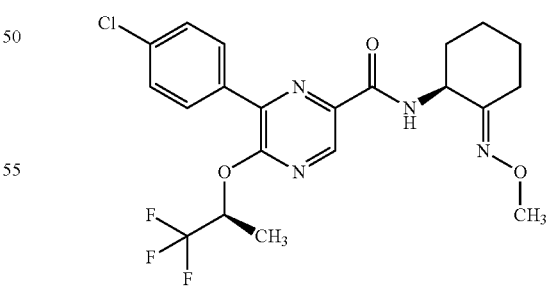

In analogy to Example 9 by substituting 4-(4-chloro-phenyl)-5-(2,2,2-trifluoro-ethoxy)-pyridine-2-carboxylic acid with (S)-6-(4-chlorophenyl)-5-(1,1,1-trifluoropropan-2-yloxy)pyrazine-2-carboxylic acid the title compound was obtained as white solid. MS (EI): 471.1 (M+H), m.p.: 120-123° C.

Example 28

4-(4-Chlorophenyl)-N-((S,E)-2-(methoxyimino)cyclohexyl)-5-((S)-1,1,1-trifluoropropan-2-yloxy)pyrimidine-2-carboxamide

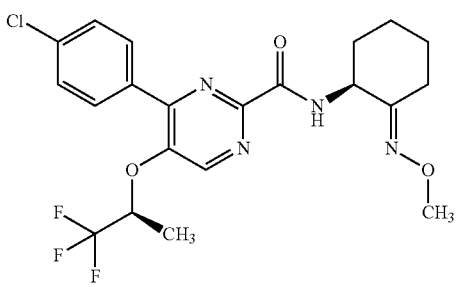 [SMILES: CO/N=C1\CCCC[C@@H]1NC(=O)c1ncc(O[C@@H](C)C(F)(F)F)c(-c2ccc(Cl)cc2)n1]

In analogy to Example 9 by substituting 4-(4-chloro-phenyl)-5-(2,2,2-trifluoro-ethoxy)-pyridine-2-carboxylic acid with 4-(4-chloro-phenyl)-5-((S)-2,2,2-trifluoro-1-methyl-ethoxy)-pyrimidine-2-carboxylic acid the title compound was obtained as white solid. MS (EI): =471.1 (M+H), m.p.: 180-182° C.

Example 28b 4-(4-Chloro-phenyl)-5-((S)-2,2,2-trifluoro-1-methyl-ethoxy)-pyrimidine-2-carboxylic acid

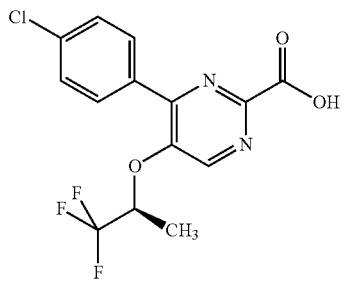 [SMILES: C[C@H](Oc1cnc(C(=O)O)nc1-c1ccc(Cl)cc1)C(F)(F)F]

The starting material 4-(4-chloro-phenyl)-5-(S)-2,2,2-trifluoro-1-methyl-ethoxy)-pyrimidine-2-carboxylic acid was obtained in analogy to example 19 by substituting cyclopropanemethanol with (S)-1,1,1-trifluoro-2-propanol as white solid MS (EI): =345.0 (M–H).

Example 29

4-(4-Chlorophenyl)-N-((S,E)-2-(methoxyimino)cyclohexyl)-5-((S)-1,1,1-trifluoropropan-2-yloxy)picolinamide

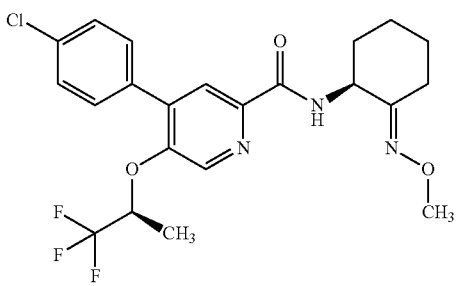 [SMILES: CO/N=C1\CCCC[C@@H]1NC(=O)c1cc(-c2ccc(Cl)cc2)c(O[C@@H](C)C(F)(F)F)cn1]

In analogy to Example 9 by substituting 4-(4-chloro-phenyl)-5-(2,2,2-trifluoro-ethoxy)-pyridine-2-carboxylic acid with (S)-4-(4-chlorophenyl)-5-(1,1,1-trifluoropropan-2-yloxy)picolinic acid the title compound was obtained as white solid. MS (EI): =470.1 (M+H), m.p.: 123-125° C.

Example 29b (S)-4-(4-Chlorophenyl)-5-(1,1,1-trifluoropropan-2-yloxy)picolinic acid

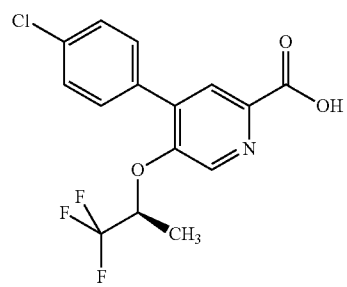 [SMILES: C[C@H](Oc1cnc(C(=O)O)cc1-c1ccc(Cl)cc1)C(F)(F)F]

The starting material (S)-4-(4-chlorophenyl)-5-(1,1,1-trifluoropropan-2-yloxy)picolinic acid was obtained in analogy to Examples 10b to 10d by substituting 6-chloro-2-(4-chlorophenyl)-3-fluoro-pyridine with 2-chloro-4-(4-chloro-phenyl)-5-fluoro-pyridine and 2,2,2-trifluoro-ethanol with (S)-1,1,1-trifluoro-2-propanol as white solid. MS (EI)=344.1 (M+H).

Example 29c

2-Chloro-4-(4-chloro-phenyl)-5-fluoro-pyridine

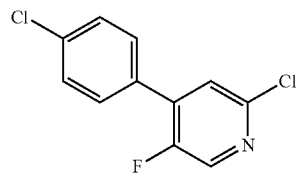 [SMILES: Fc1cnc(Cl)cc1-c1ccc(Cl)cc1]

The intermediate 2-chloro-4-(4-chloro-phenyl)-5-fluoro-pyridine was obtained in analogy to Example 19e by substituting 2,4-dichloro-5-fluoropyrimidine with 4-bromo-2-chloro-5-fluoro-pyridine as white solid MS (EI)=241 and 243 (M+).

Example 30

5-(4-Chlorophenyl)-N-((S,E)-2-(methoxyimino)cyclohexyl)-6-((S)-1,1,1-trifluoropropan-2-yloxy)nicotinamide

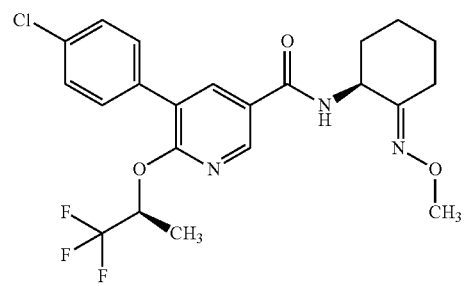 [SMILES: CO/N=C1\CCCC[C@@H]1NC(=O)c1cnc(O[C@@H](C)C(F)(F)F)c(-c2ccc(Cl)cc2)c1]

In analogy to Example 9 the title compound 5-(4-chlorophenyl)-N-((S,E)-2-(methoxyimino)cyclohexyl)-6-((S)-1,1,1-trifluoropropan-2-yloxy)nicotinamide was obtained by substituting 4-(4-chloro-phenyl)-5-(2,2,2-trifluoro-ethoxy)-pyridine-2-carboxylic acid with (S)-5-(4-chlorophenyl)-6-(1,1,1-trifluoropropan-2-yloxy)nicotinic acid as white solid. MS (EI)=470.1 (M+H), m.p.: 119-121° C.

Example 30b (S)-5-(4-Chlorophenyl)-6-(1,1,1-trifluoropropan-2-yloxy)nicotinic acid

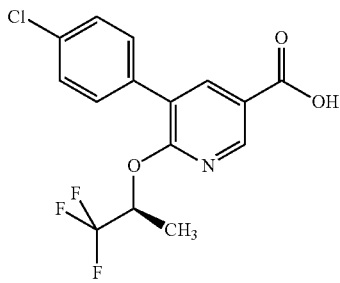 [SMILES: C[C@H](Oc1ncc(C(=O)O)cc1-c1ccc(Cl)cc1)C(F)(F)F]

The starting material (S)-5-(4-chlorophenyl)-6-(1,1,1-trifluoropropan-2-yloxy)nicotinic acid was obtained in analogy to Example 10b to 10d by substituting 2,4-chloro-5-fluoropyridine with 3-bromo-5-chloro-2-fluoropyridine as white solid. MS (EI)=344.1 (M−H).

Example 31

5-(4-Chloro-phenyl)-N-{2-cyclopropyl-2-[(E)-methoxyimino]-ethyl}-6-((S)-2,2,2-trifluoro-1-methyl-ethoxy)-nicotinamide

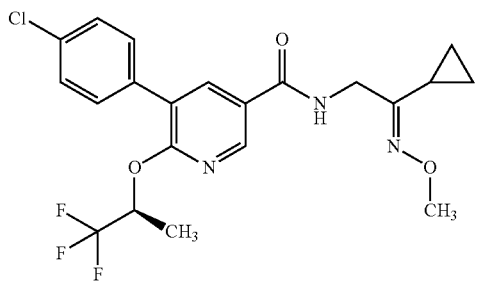 [SMILES: CO/N=C(/CNC(=O)c1cnc(O[C@@H](C)C(F)(F)F)c(-c2ccc(Cl)cc2)c1)C1CC1]

The title compound 5-(4-chloro-phenyl)-N-{2-cyclopropyl-2-[(E)-methoxyimino]-ethyl}-6-((S)-2,2,2-trifluoro-1-methyl-ethoxy)-nicotinamide was obtained in analogy to example 12 by substituting 5-(3,4-dichloro-phenyl)-6-(2,2,2-trifluoro-ethoxy)-nicotinic acid with (S)-5-(4-chlorophenyl)-6-(1,1,1-trifluoropropan-2-yloxy)nicotinic acid as white solid. MS (EI)=456.1 (M+H). M.p.: 103-106° C.

Example 32

(E)-4-(4-chlorophenyl)-N-(2-cyclopropyl-2-(methoxyimino)ethyl)-5-(2,2,2-trifluoroethoxy)picolinamide

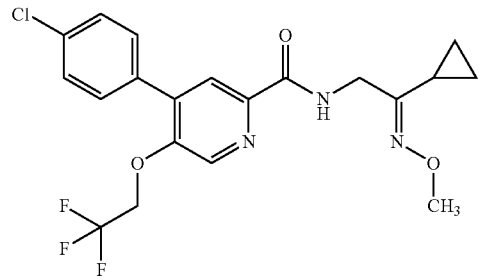 [SMILES: CO/N=C(/CNC(=O)c1cc(-c2ccc(Cl)cc2)c(OCC(F)(F)F)cn1)C1CC1]

The title compound (E)-4-(4-chlorophenyl)-N-(2-cyclopropyl-2-(methoxyimino)ethyl)-5-(2,2,2-trifluoroethoxy)picolinamide was obtained as white solid in analogy to example 9 by substituting (S)-2-amino-cyclohexanone-(E)-O-methyl-oxime hydrochloride with (E)-2-amino-1-cyclopropylethanone O-methyl oxime hydrochloride; MS (EI)=442.1 (M+H).

The invention claimed is:
1. A compound according to formula I,

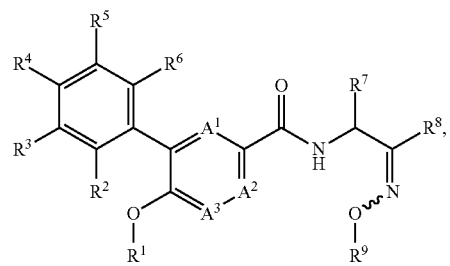

wherein
A$^1$, A$^2$ and A$^3$ are each individually selected from N and CH, provided that at least one of A$^1$, A$^2$ or A$^3$ is N and at least one of A$^1$, A$^2$ or A$^3$ is CH;
R$^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;

R² and R⁶ independently from each other are hydrogen or halogen;

R³ and R⁵ independently from each other are selected from the group consisting of hydrogen, lower alkyl, lower alkoxy, halogen, lower halogenalkyl, lower halogenalkoxy and cyano;

R⁴ is selected from the group consisting of hydrogen, lower alkoxy, halogen, lower halogenalkyl, lower halogenalkoxy and cyano;

R⁷ and R⁸ together with the C atoms to which they are attached form a cycloalkyl ring, or R⁷ is hydrogen and R⁸ is lower halogenalkyl or cycloalkyl; and R⁹ is selected from the group consisting of hydrogen, lower alkyl, lower halogenalkyl, lower alkoxyalkyl and lower carbamoylalkyl;

or a pharmaceutically acceptable salt thereof.

2. A compound according to claim 1, wherein R¹ is lower cycloalkylalkyl or lower halogenalkyl.

3. A compound according to claim 1, wherein R¹ is lower halogenalkyl.

4. A compound according to claim 1, wherein R² and R⁶ are hydrogen.

5. A compound according to claim 1, wherein R³ and R⁵ are independently from each other hydrogen or halogen.

6. A compound according to claim 1, wherein R⁴ is halogen.

7. A compound according to claim 1, wherein R⁷ and R⁸ together with the C atoms to which they are attached form a cyclohexyl ring.

8. A compound according to claim 1, wherein R⁷ is hydrogen and R⁸ is lower halogenalkyl or cycloalkyl.

9. A compound according to claim 1, wherein R⁹ is selected from the group consisting of lower alkyl, lower halogenalkyl, lower alkoxyalkyl and lower carbamoylalkyl.

10. A compound according to claim 1, wherein R⁹ is lower alkyl.

11. A compound according to claim 10, wherein A³ is N and A¹ and A² are CH.

12. A compound according to claim 1, selected from the group consisting of 5-(4-chloro-phenyl)-6-cyclopropylmethoxy-N-{(S)-2-[(E)-methoxyimino]-cyclohexyl}-nicotinamide, 5-(4-chloro-phenyl)-N-{(S)-2-[(E)-methoxyimino]-cyclohexyl}-6-(2,2,2-trifluoro-ethoxy)-nicotinamide, 5-(4-chloro-phenyl)-6-cyclopropylmethoxy-N-{(S)-2-[(E)-isopropoxyimino]-cyclohexyl}-nicotinamide, 5-(4-chloro-phenyl)-6-cyclopropylmethoxy-N-{(S)-2-[(E)-2,2,2-trifluoro-ethoxyimino]-cyclohexyl}-nicotinamide, N-{(S)-2-[(E)-carbamoylmethoxyimino]-cyclohexyl}-5-(4-chloro-phenyl)-6-cyclopropylmethoxy-nicotinamide, 5-(4-chloro-phenyl)-6-cyclopropylmethoxy-N-{(S)-2-[(E)-methoxymethoxyimino]-cyclohexyl}-nicotinamide, 5-(3,4-dichloro-phenyl)-N-{(S)-2-[(E)-methoxyimino]-cyclohexyl}-6-(2,2,2-trifluoro-ethoxy)-nicotinamide, 5-(3,4-dichloro-phenyl)-N-{(R)-2-[(E)-methoxyimino]-cyclohexyl}-6-(2,2,2-trifluoro-ethoxy)-nicotinamide, 4-(4-chloro-phenyl)-5-(2,2,2-trifluoro-ethoxy)-pyridine-2-carboxylic acid {(S)-2-[(E)-methoxyimino]-cyclohexyl}-amide, 6-(4-chloro-phenyl)-5-(2,2,2-trifluoro-ethoxy)-pyridine-2-carboxylic acid {(S)-2-[(E)-methoxyimino]-cyclohexyl}-amide, and pharmaceutically-acceptable salts thereof.

13. A compound according to claim 1, selected from the group consisting of

N-(E)-(2-cyclopropyl-2-hydroxyimino-ethyl)-5-(3,4-dichloro-phenyl)-6-(2,2,2-trifluoro-ethoxy)-nicotinamide, N-{2-cyclopropyl-2-[(E)-methoxyimino]-ethyl}-5-(3,4-dichloro-phenyl)-6-(2,2,2-trifluoro-ethoxy)-nicotinamide, 5-(4-chloro-phenyl)-N-{2-cyclopropyl-2-[(Z)-methoxyimino]-ethyl}-6-(2,2,2-trifluoro-ethoxy)-nicotinamide, 5-(4-chloro-phenyl)-N-{2-cyclopropyl-2-[(E)-methoxyimino]-ethyl}-6-(2,2,2-trifluoro-ethoxy)-nicotinamide, 5-(3,4-dichloro-phenyl)-6-(2,2,2-trifluoro-ethoxy)-N-{3,3,3-trifluoro-2-[(Z)-methoxyimino]-propyl}-nicotinamide, 5-(4-chloro-phenyl)-6-(2,2,2-trifluoro-ethoxy)-pyridazine-3-carboxylic acid {(R)-2-[(E)-methoxyimino]-cyclohexyl}-amide, 5-(4-chloro-phenyl)-6-(2,2,2-trifluoro-ethoxy)-pyridazine-3-carboxylic acid {(S)-2-[(E)-methoxyimino]-cyclohexyl}-amide, 5-(4-chloro-phenyl)-6-cyclopropylmethoxy-pyridazine-3-carboxylic acid {(S)-2-[(E)-methoxyimino]-cyclohexyl}-amide, 4-(4-chloro-phenyl)-5-cyclopropylmethoxy-pyrimidine-2-carboxylic acid {2-cyclopropyl-2-[(Z)-methoxyimino]-ethyl}-amide, 4-(4-chloro-phenyl)-5-cyclopropylmethoxy-pyrimidine-2-carboxylic acid {2-cyclopropyl-2-[(E)-methoxyimino]-ethyl}-amide, and pharmaceutically acceptable salts thereof.

14. A compound according to claim 1, selected from the group consisting of 6-(4-chloro-phenyl)-5-(2,2,2-trifluoro-ethoxy)-pyridine-2-carboxylic acid {3,3,3-trifluoro-2-[(Z)-methoxyimino]-propyl}-amide, N-{2-cyclopropyl-2-[(E/Z)-2,2,2-trifluoro-ethoxyimino]-ethyl}-5-(3,4-dichloro-phenyl)-6-(2,2,2-trifluoro-ethoxy)-nicotinamide, (E)-N-(2-cyclopropyl-2-(methoxyimino)ethyl)-5-(3,4-dichlorophenyl)-6-(2,2,2-trifluoroethoxy)pyridazine-3-carboxamide, 5-(3,4-dichloro-phenyl)-6-(2,2,2-trifluoro-ethoxy)-pyridazine-3-carboxylic acid {(S)-2-[(E)-methoxyimino]-cyclohexyl}-amide, (S,E)-5-(4-chlorophenyl)-N-(2-cyclopropyl-2-(methoxyimino)ethyl)-6-(1,1,1-trifluoropropan-2-yloxy)pyridazine-3-carboxamide, (S,E)-6-(4-chlorophenyl)-N-(2-cyclopropyl-2-(methoxyimino)ethyl)-5-(1,1,1-trifluoropropan-2-yloxy)pyrazine-2-carboxamide, 6-(4-chlorophenyl)-N-((S,E)-2-(methoxyimino)cyclohexyl)-5-((S)-1,1,1-trifluoropropan-2-yloxy)pyrazine-2-carboxamide, 4-(4-chlorophenyl)-N-((S,E)-2-(methoxyimino)cyclohexyl)-5-((S)-1,1,1-trifluoropropan-2-yloxy)pyrimidine-2-carboxamide, 4-(4-chlorophenyl)-N-((S,E)-2-(methoxyimino)cyclohexyl)-5-((S)-1,1,1-trifluoropropan-2-yloxy)picolinamide, 5-(4-chlorophenyl)-N-((S,E)-2-(methoxyimino)cyclohexyl)-6-((S)-1,1,1-trifluoropropan-2-yloxy)nicotinamide, 5-(4-chloro-phenyl)-N-{2-cyclopropyl-2-[(E)-methoxyimino]-ethyl}-6-((S)-2,2,2-trifluoro-1-methyl-ethoxy)-nicotinamide, (E)-4-(4-chlorophenyl)-N-(2-cyclopropyl-2-(methoxyimino)ethyl)-5-(2,2,2-trifluoroethoxy)picolinamide, and pharmaceutically acceptable salts thereof.

15. A pharmaceutical composition comprising a compound according to a claim 1 and a pharmaceutically acceptable carrier and/or adjuvant.

16. A compound according to formula I,

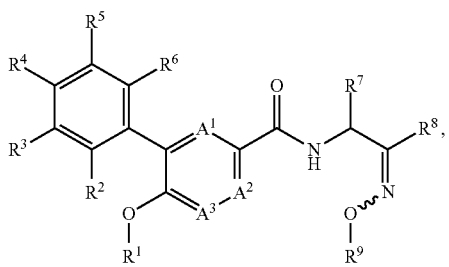

wherein
two of $A^1$, $A^2$ and $A^3$ are N and the other is CH;
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy and cyano;
$R^7$ and $R^8$ together with the C atoms to which they are attached form a cycloalkyl ring, or
$R^7$ is hydrogen and $R^8$ is lower halogenalkyl or cycloalkyl; and
$R^9$ is selected from the group consisting of hydrogen, lower alkyl, lower halogenalkyl, lower alkoxyalkyl and lower carbamoylalkyl;
or a pharmaceutically acceptable salt thereof.

17. The compound of claim 16 wherein said compound is 6-(4-chlorophenyl)-N-(2-cyclopropyl-2-(methoxyimino) ethyl)-5-(1,1,1-trifluoropropan-2-yloxy)pyrazine-2-carboxamide or a pharmaceutically acceptable salt thereof.

18. The compound of claim 16 wherein said compound is 4-(4-chlorophenyl)-N-(2-(methoxyimino)cyclohexyl)-5-(1, 1,1-trifluoropropan-2-yloxy)pyrimidine-2-carboxamide or a pharmaceutically acceptable salt thereof.

19. The compound of claim 16 wherein said compound is N-(2-cyclopropyl-2-(methoxyimino)ethyl)-5-(3,4-dichlorophenyl)-6-(2,2,2-trifluoroethoxy)pyridazine-3-carboxamide or a pharmaceutically acceptable salt thereof.

20. A compound according to formula I,

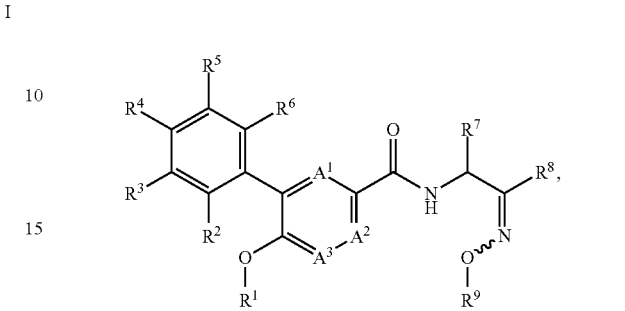

wherein
one of $A^1$, $A^2$ and $A^3$ is nitrogen and the others are CH;
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy and cyano;
$R^7$ and $R^8$ together with the C atoms to which they are attached form a cycloalkyl ring, or
$R^7$ is hydrogen and $R^8$ is lower halogenalkyl or cycloalkyl; and
$R^9$ is selected from the group consisting of hydrogen, lower alkyl, lower halogenalkyl, lower alkoxyalkyl and lower carbamoylalkyl;
or a pharmaceutically acceptable salt thereof.

21. The compound of claim 20 wherein said compound is 5-(4-chlorophenyl)-N-(2-(methoxyimino)cyclohexyl)-6-1,1, 1-trifluoropropan-2-yloxy)nicotinamide or a pharmaceutically acceptable salt thereof.

* * * * *